(12) United States Patent
Jia et al.

(10) Patent No.: US 12,299,879 B2
(45) Date of Patent: May 13, 2025

(54) SYSTEM AND METHOD FOR MEDICAL IMAGING OF INTERVERTEBRAL DISCS

(71) Applicant: SHANGHAI UNITED IMAGING HEALTHCARE CO., LTD., Shanghai (CN)

(72) Inventors: Fenggang Jia, Shanghai (CN); Wenjun Yu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 366 days.

(21) Appl. No.: 17/809,267

(22) Filed: Jun. 27, 2022

(65) Prior Publication Data

US 2022/0327703 A1 Oct. 13, 2022

Related U.S. Application Data

(63) Continuation of application No. PCT/CN2020/139660, filed on Dec. 25, 2020.

(30) Foreign Application Priority Data

Dec. 25, 2019 (CN) .......................... 201911355722.8

(51) Int. Cl.
*G06T 7/00* (2017.01)
*A61B 6/00* (2024.01)
(Continued)

(52) U.S. Cl.
CPC ............ *G06T 7/0012* (2013.01); *A61B 6/032* (2013.01); *A61B 6/505* (2013.01); *A61B 6/5217* (2013.01);
(Continued)

(58) Field of Classification Search
CPC ......... G06T 7/0012; G06T 2207/10081; G06T 2207/10088; G06T 2207/30012;
(Continued)

(56) References Cited

U.S. PATENT DOCUMENTS

2007/0127799 A1 6/2007 Reisman et al.
2012/0053454 A1* 3/2012 Wang ..................... A61B 6/505
600/425
(Continued)

FOREIGN PATENT DOCUMENTS

CN 105405129 A 3/2016
CN 106157288 A 11/2016
(Continued)

OTHER PUBLICATIONS

International Search Report in PCT/CN2020/139660 mailed on Mar. 24, 2021, 5 pages.
(Continued)

*Primary Examiner* — Wassim Mahrouka
(74) *Attorney, Agent, or Firm* — METIS IP LLC

(57) ABSTRACT

The present disclosure directs to a method for image processing. The method may include obtaining scanning data of a spine of a subject, determining one or more centrum parameters of each of a plurality of centrums of the spine based on the scanning data, and identifying at least one intervertebral disc based on the one or more centrum parameters. Each of the at least one intervertebral disc may be between a pair of neighboring centrums of the plurality of centrums. The method may include determining an intervertebral disc reconstruction protocol of each of the at least one intervertebral disc, determining a target intervertebral disc of the at least one intervertebral disc, and reconstructing one or more images of the target intervertebral disc based on an intervertebral disc reconstruction protocol of the target
(Continued)

intervertebral disc. The intervertebral disc reconstruction protocols may relate to MPR.

20 Claims, 14 Drawing Sheets

(51) Int. Cl.
*A61B 6/03* (2006.01)
*A61B 6/50* (2024.01)
*G16H 30/20* (2018.01)
*G16H 50/20* (2018.01)

(52) U.S. Cl.
CPC .............. *G16H 30/20* (2018.01); *G16H 50/20* (2018.01); *G06T 2207/10081* (2013.01); *G06T 2207/10088* (2013.01); *G06T 2207/30012* (2013.01)

(58) Field of Classification Search
CPC ....... A61B 6/032; A61B 6/5217; A61B 5/004; A61B 5/4514; A61B 6/461; A61B 5/055; A61B 5/4566; A61B 6/505; A61B 6/466; A61B 2576/02; G16H 30/20; G16H 50/20
See application file for complete search history.

(56) References Cited

U.S. PATENT DOCUMENTS

| | | | |
|---|---|---|---|
| 2012/0172700 A1* | 7/2012 | Krishnan | A61B 6/505 600/407 |
| 2015/0248593 A1 | 9/2015 | Nakashima et al. | |
| 2016/0078615 A1 | 3/2016 | Zhan et al. | |
| 2016/0267655 A1 | 9/2016 | Akahori | |
| 2019/0035085 A1 | 1/2019 | Yu | |
| 2019/0192099 A1 | 6/2019 | Jia et al. | |
| 2021/0327063 A1* | 10/2021 | Prasad | G06T 7/11 |

FOREIGN PATENT DOCUMENTS

| | | |
|---|---|---|
| CN | 107085860 A | 8/2017 |
| CN | 109615656 A | 4/2019 |
| CN | 110599508 A | 12/2019 |
| WO | 2021129842 A1 | 7/2021 |

OTHER PUBLICATIONS

Written Opinion in PCT/CN2020/139660 mailed on Mar. 24, 2021, 5 pages.

Anjany Sekuboyina et al., Labelling Vertebrae with 2D Reformations of Multidetector CT Images: An Adversarial Approach for Incorporating Prior Knowledge of Spine Anatomy, Radiology: Artificial Intelligence, 2(2): 1-9, 2020.

Fausto Milletari et al., V-Net: Fully Convolutional Neural Networks for Volumetric Medical Image Segmentation, 2016 Fourth International Conference on 3D Vision, 2016, 7 pages.

A.Hennemuth et al., Fast Interactive Exploration of 4D MRI Flow Data, Proc. of SPIE, 7964: e1-e11, 2011.

Ji, Xing et al., Fully Automatic Localization and Segmentation of Intervertebral Disc from 3D Multi-modality MR Images by Regression Forest and CNN, 18th International Conference, Lecture Notes Incomputer Science Lect Notes Computer, 92-101, 2016.

Amir Jamaludin et al., Automatic Intervertebral Discs Localization and Segmentation: A Vertebral Approach, 18th International Conference, Lecture Notes Incomputer Science Lect Notes Computer, 97-103, 2016.

The Extended European Search Report in European Application No. 20905327.1 mailed on Apr. 25, 2023, 15 pages.

Wu, Jian et al., Advance in Spinal Image Segmentation and Registration(review), Chinese Journal of Rehabilitation Theory and Practice, 16(2): 130-133, 2010.

* cited by examiner

700

```
┌─────────────────────────────────────────────────┐
│ Determining at least one region in one or more  │      710
│ images of the spine, each of the at least one   │ ∿
│ region including an intervertebral disc         │
└─────────────────────────────────────────────────┘
                        │
                        ▼
┌─────────────────────────────────────────────────┐
│ Identifying an intervertebral disc from each of │      720
│ the at least one region                         │ ∿
└─────────────────────────────────────────────────┘
```

FIG. 7A

```
┌─────────────────────────────────────────────────┐
│ Determining one or more intervertebral disc     │      750
│ parameters of each of the at least one          │ ∿
│ intervertebral disc                             │
└─────────────────────────────────────────────────┘
                        │
                        ▼
┌─────────────────────────────────────────────────┐
│ Determining an intervertebral disc              │      760
│ reconstruction protocol of each of the at least │ ∿
│ one intervertebral disc based on image          │
│ reconstruction parameters and the one or more   │
│ intervertebral disc parameters of the each      │
│ intervertebral disc                             │
└─────────────────────────────────────────────────┘
```

FIG. 7B

 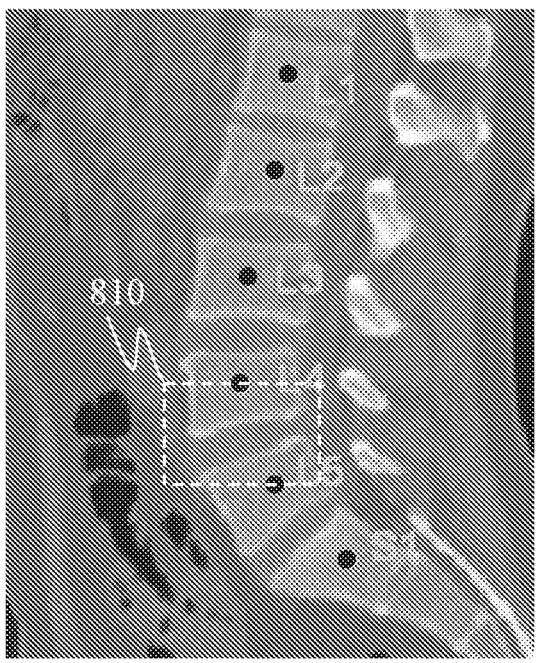
FIG. 8A　　　　　　　　　　FIG. 8B
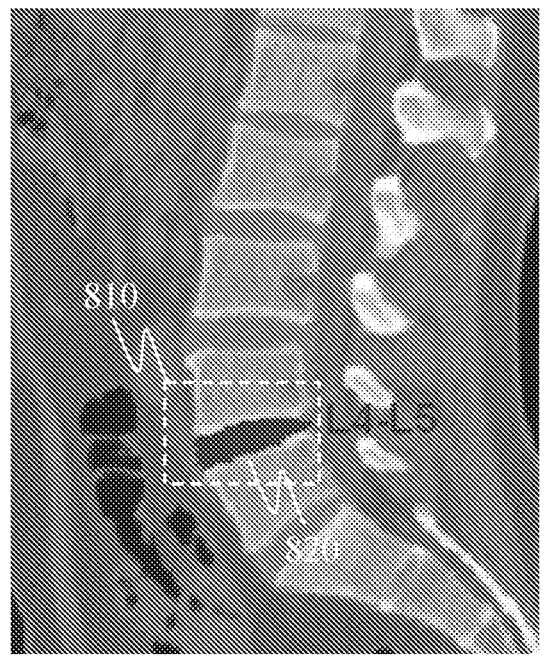
FIG. 8C

SYSTEM AND METHOD FOR MEDICAL IMAGING OF INTERVERTEBRAL DISCS

CROSS-REFERENCE TO RELATED APPLICATIONS

This application is a continuation of International Application No. PCT/CN2020/139660, filed on Dec. 25, 2020, which claims priority of Chinese Patent Application No. 201911355722.8, filed on Dec. 25, 2019, the contents of which are hereby incorporated by reference.

TECHNICAL FIELD

The present disclosure generally relates to medical imaging, and more particularly to a system and method for imaging of intervertebral discs of a spine of a subject.

BACKGROUND

Computed tomography (CT) is a technology that makes use of a computer-processed combination of X-ray images taken from different angles to produce one or more transverse images. The CT technology has been widely used in medical diagnosis. However, a CT image, such as a CT tomographic image, may not satisfy clinical needs for diagnosis of intervertebral discs since bodies of different patients vary in multiple aspects including, for example, spinal curvature, sizes of intervertebral discs, directions of intervertebral discs, etc. Thus, it is desirable to develop a system and method for imaging of intervertebral discs more accurately and efficiently.

SUMMARY

According to one aspect of the present disclosure, a method implemented on a computing device having a processor and a computer-readable storage device is provided. The method may include obtaining scanning data of a spine of a subject. The method may also include determining one or more centrum parameters of each of a plurality of centrums of the spine based on the scanning data and identifying at least one intervertebral disc based on the one or more centrum parameters of each of the plurality of centrums. Each of the at least one intervertebral disc may be between a pair of neighboring centrums of the plurality of centrums. The method may also include determining an intervertebral disc reconstruction protocol of each of the at least one intervertebral disc and determining a target intervertebral disc of the at least one intervertebral disc. The intervertebral disc reconstruction protocols of the at least one intervertebral disc may relate to multi-planar reconstruction (MPR). The method may further include reconstructing one or more images of the target intervertebral disc based on an intervertebral disc reconstruction protocol of the target intervertebral disc.

In some embodiments, the scanning data may include computed tomography (CT) data or magnetic resonance (MR) data.

In some embodiments, the one or more centrum parameters of each of the plurality of centrums of the spine may include a center point and a label of the centrum.

In some embodiments, the determining an intervertebral disc reconstruction protocol of each of the at least one intervertebral disc may include, for each of the at least one intervertebral disc, determining one or more intervertebral disc parameters of the intervertebral disc and determining the intervertebral disc reconstruction protocol of the intervertebral disc based on image reconstruction parameters and the one or more intervertebral disc parameters of the intervertebral disc.

In some embodiments, the determining one or more intervertebral disc parameters of the intervertebral disc may include obtaining coordinates of elements of the intervertebral disc, determining a center point, at least two directions, and a range of the intervertebral disc based on the coordinates of elements of the intervertebral disc, and determining a label of the intervertebral disc based on labels of a pair of neighboring centrums. The intervertebral disc may be located between the pair of neighboring centrums.

In some embodiments, the intervertebral disc reconstruction protocol of each of the at least one intervertebral disc may relate to at least one of the label, the range, the center point, or the at least two directions of the intervertebral disc, a slice thickness, a slice count, or a reconstruction dimension.

In some embodiments, the method may include determining whether the intervertebral disc reconstruction protocol of each of the at least one intervertebral disc satisfies a verification condition, and in response to determining that the intervertebral disc reconstruction protocol of an intervertebral disc does not satisfy the verification condition, updating the intervertebral disc reconstruction protocol of the intervertebral disc.

In some embodiments, the method may include transmitting the reconstructed images of the target intervertebral disc to a terminal device, receiving diagnosis information from the terminal device, and generating a report regarding the target intervertebral disc based on the diagnosis information and the reconstructed images of the target intervertebral disc.

According to another aspect of the present disclosure, a system is provided. The system may include at least one storage medium including a set of instructions and at least one processor configured to communicate with the at least one storage medium. When executing the set of instructions, the at least one processor may be configured to direct the system to perform the following operations. The at least one processor may be configured to direct the system to obtain scanning data of a spine of a subject. The at least one processor may be configured to direct the system to determine one or more centrum parameters of each of a plurality of centrums of the spine based on the scanning data, and identify at least one intervertebral disc based on the one or more centrum parameters of each of the plurality of centrums. Each of the at least one intervertebral disc may be between a pair of neighboring centrums of the plurality of centrums. The at least one processor may be configured to direct the system to determine an intervertebral disc reconstruction protocol of each of the at least one intervertebral disc, and determine a target intervertebral disc of the at least one intervertebral disc. The intervertebral disc reconstruction protocols of the at least one intervertebral disc may relate to multi-planar reconstruction (MPR). The at least one processor may be configured to direct the system to reconstruct one or more images of the target intervertebral disc based on an intervertebral disc reconstruction protocol of the target intervertebral disc.

According to a further aspect of the present disclosure, a non-transitory readable medium including at least one set of instructions is provided. When executed by at least one processor of a computing device, the at least one set of instructions may direct the at least one processor to perform a method. The method may include obtaining scanning data of a spine of a subject. The method may also include determining one or more centrum parameters of each of a plurality of centrums of the spine based on the scanning data and identifying at least one intervertebral disc based on the one or more centrum parameters of each of the plurality of centrums. Each of the at least one intervertebral disc may be between a pair of neighboring centrums of the plurality of centrums. The method may also include determining an intervertebral disc reconstruction protocol of each of the at least one intervertebral disc and determining a target intervertebral disc of the at least one intervertebral disc. The intervertebral disc reconstruction protocols of the at least one intervertebral disc may relate to multi-planar reconstruction (MPR). The method may further include reconstructing one or more images of the target intervertebral disc based on an intervertebral disc reconstruction protocol of the target intervertebral disc.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 7A is a flowchart illustrating an exemplary process for identify at least one intervertebral disc according to some embodiments of the present disclosure;

FIG. 7B is a flowchart illustrating an exemplary process for determining an intervertebral disc reconstruction protocol of each of the at least one intervertebral disc according to some embodiments of the present disclosure;

FIGS. 8A and 8B illustrate an exemplary sagittal view of a portion of a spine of a subject according to some embodiments of the present disclosure;

FIG. 8C illustrates an exemplary intervertebral disc identified by segmenting a region that accommodates the intervertebral disc;

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by other expression if they achieve the same purpose.

Figure 2:
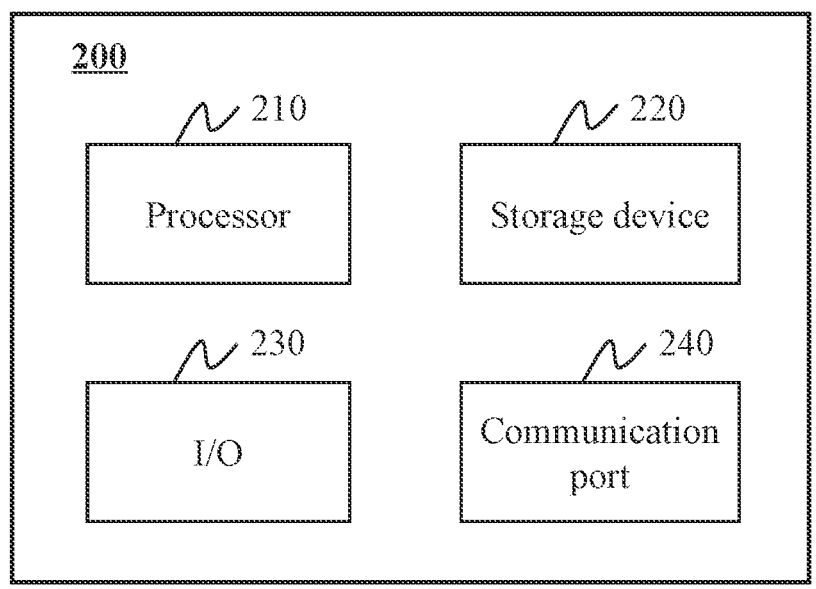
FIG. 2 is a schematic diagram illustrating exemplary hardware and/or software components of an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

The flowcharts used in the present disclosure illustrate operations that systems implement according to some embodiments of the present disclosure. It is to be expressly understood the operations of the flowcharts may be implemented not in order. Conversely, the operations may be implemented in an inverted order, or simultaneously. Moreover, one or more other operations may be added to the flowcharts. One or more operations may be removed from the flowcharts.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and methods for non-invasive imaging, such as for disease diagnosis, treatment, and/or research purposes. In some embodiments, the imaging system may include a single modality system and/or a multi-modality system. The term "modality" used herein broadly refers to an imaging or treatment method or technology that gathers, generates, processes, and/or analyzes imaging information of a subject or treatments the subject. The single modality system may include a computed tomography (CT) system, a magnetic resonance imaging (MRI) system, an ultrasound imaging system, an X-ray imaging system, an ultrasonography system, a positron emission tomography (PET) system, an optical coherence tomography (OCT) imaging system, an ultrasound (US) imaging system, an intravascular ultrasound (IVUS) imaging system, a near-infrared spectroscopy (NIRS) imaging system, or the like, or any combination thereof. The multi-modality system may include an X-ray imaging-magnetic resonance imaging (X-ray-MM) system, a positron emission tomography-X-ray imaging (PET-X-ray) system, a single-photon emission computed tomography-magnetic resonance imaging (SPECT-MRI) system, a positron emission tomography-computed tomography (PET-CT) system, a C-arm system, a positron emission tomography-magnetic resonance imaging (PET-MR) system, a digital subtraction angiography-magnetic resonance imaging (DSA-MRI) system, or the like, or any combination thereof.

In the present disclosure, the term "image" may refer to a two-dimensional (2D) image, a three-dimensional (3D) image, or a four-dimensional (4D) image. In some embodiments, the term "image" may refer to an image of a region (e.g., a region of interest (ROI)) of a subject. As described above, the image may be a CT image, a PET image, an MR image, a fluoroscopy image, an ultrasound image, an Electronic Portal Imaging Device (EPID) image, etc.

As used herein, a representation of a subject (e.g., a patient, or a portion thereof) in an image may be referred to as the subject for brevity. For instance, a representation of an organ or tissue (e.g., the heart, the liver, a lung, etc., of a patient) in an image may be referred to as the organ or tissue for brevity. An image including a representation of a subject may be referred to as an image of the subject or an image including the subject for brevity. As used herein, an operation on a representation of a subject in an image may be referred to as an operation on the subject for brevity. For instance, a segmentation of a portion of an image including a representation of an organ or tissue (e.g., the heart, the liver, a lung, etc., of a patient) from the image may be referred to as a segmentation of the organ or tissue for brevity.

According to an aspect of the present disclosure, the disclosure is directed to systems and methods for imaging of intervertebral discs of a spine of a subject. To reconstruct an image of a target intervertebral disc, one or more centrum parameters of each of a plurality of centrums of the spine may be determined based on the scanning data. At least one intervertebral disc of the spine may be identified based on the one or more centrum parameters of each of the plurality of centrums. An intervertebral disc reconstruction protocol of each of the at least one intervertebral dis may relate to multi-planar reconstruction (MPR). The image of the target intervertebral disc may be reconstructed based on an intervertebral disc reconstruction protocol of the target intervertebral disc. In such embodiments, a plane on which the vertebral disc is located and the range of each vertebral disc may be determined according to the intervertebral disc reconstruction protocols. Images of the intervertebral discs may be reconstructed with respect to the corresponding planes in the ranges according to a multi-planar reconstruction (MPR) technique. Thus, the imaging of the intervertebral discs of the spine may be fulfilled accurately and efficiently.

Figure 1:
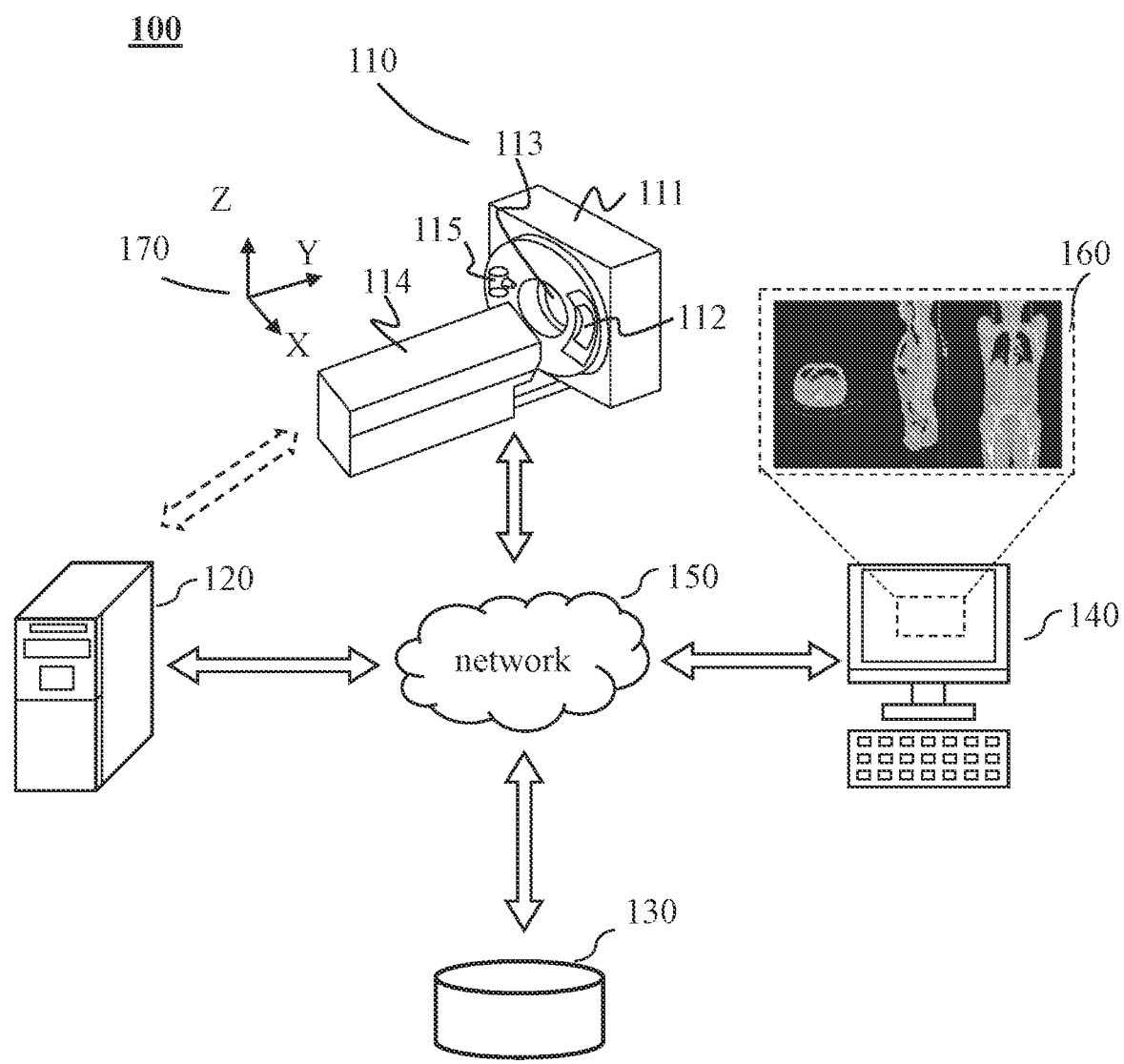
FIG. 1 is a schematic diagram illustrating an exemplary imaging system according to some embodiments of the present disclosure.

FIG. 1 is a schematic diagram illustrating an exemplary imaging system according to some embodiments of the present disclosure. As illustrated in FIG. 1, the imaging system 100 may include a scanner 110, a processing device 120, a storage device 130, a terminal device 140, and a network 150. In some embodiments, two or more components of the imaging system 100 may be connected to and/or communicate with each other via a wireless connection, a wired connection, or a combination thereof. The connection among the components of the imaging system 100 may be variable. Merely by way of example, the scanner 110 may be connected to the processing device 120 through the network 150 or directly. As another example, the storage device 130 may be connected to the processing device 120 through the network 150 or directly.

The scanner 110 may be configured to scan a subject or a portion thereof that is located within its detection region and generate scanning data/signals relating to the (portion of) subject.

In some embodiments, the scanner 110 may include a single modality device. For example, the scanner 110 may include a CT scanner, a PET scanner, a SPECT scanner, an MR scanner, an ultrasonic scanner, an ECT scanner, or the like, or a combination thereof. In some embodiment, the scanner 110 may be a multi-modality device. For example, the scanner 110 may include a PET-CT scanner, a PET-MR scanner, or the like, or a combination thereof. The following descriptions are provided, unless otherwise stated expressly, with reference to a CT scanner for illustration purposes and not intended to be limiting.

As illustrated, the CT scanner may include a gantry 111, a detector 112, a detecting region 113, a table 114, and a radiation source 115. The gantry 111 may support the detector 112 and the radiation source 115. The subject may be placed on the table 114 for scanning. The radiation source 115 may emit x-rays. The x-rays may be emitted from a focal spot using a high-intensity magnetic field to form an x-ray beam. The x-ray beam may travel toward the subject. The detector 112 may detect x-ray photons from the detecting region 113. In some embodiments, the detector 112 may include one or more detector units. The detector unit(s) may be and/or include single-row detector elements and/or multi-row detector elements.

Figure 14:
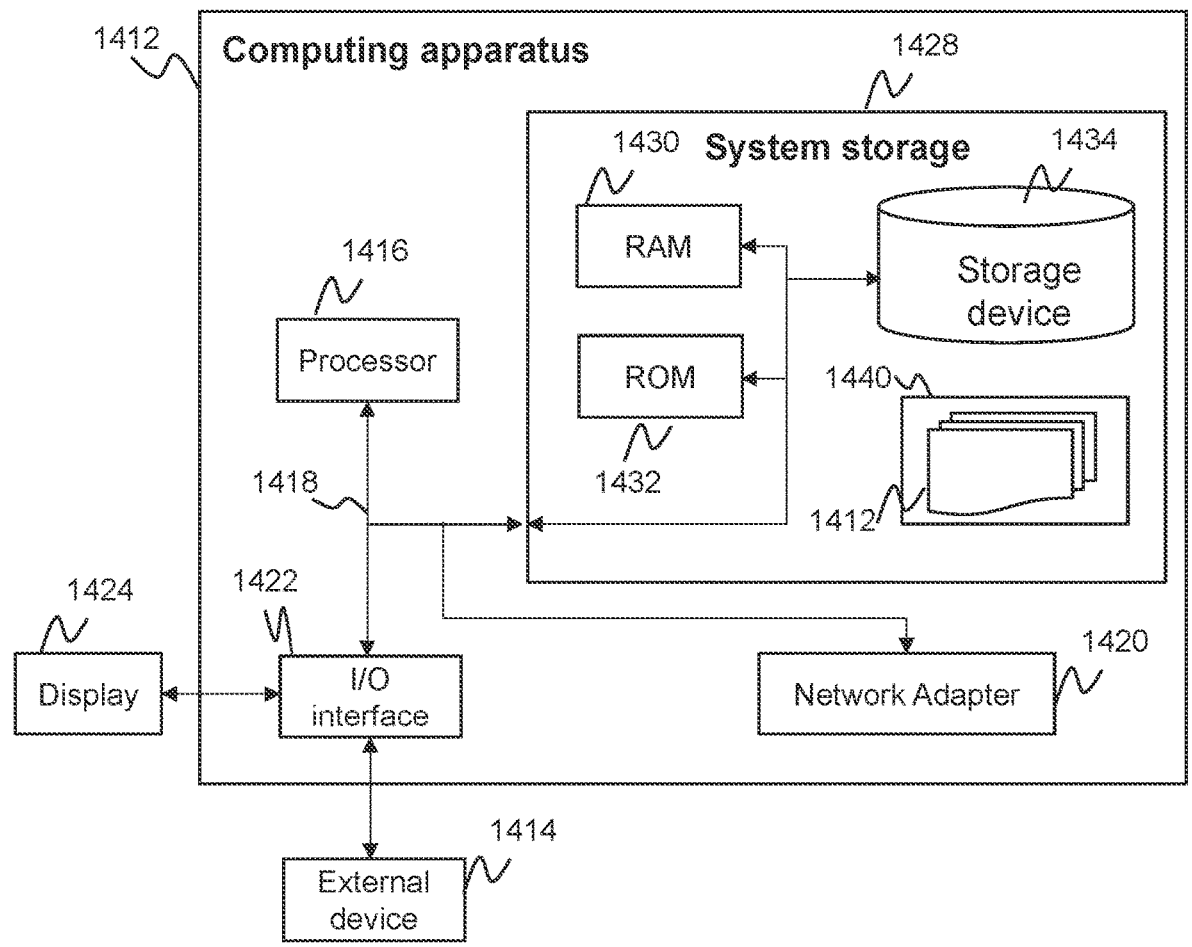
FIG. 14 is a schematic diagram of an exemplary processing device according to some embodiments of the present disclosure.

The processing device 120 may process data and/or information. The data and/or information may be obtained from the scanner 110 or retrieved from the storage device 130, the terminal device 140, and/or an external device (external to the imaging system 100) via the network 150. For example, the processing device 120 may process the data and/or information obtained from the scanner 110, and reconstruct a CT image based on the processed data and/or information. In some embodiments, the processing device 120 may be a single server or a server group. The server group may be centralized or distributed. In some embodiments, the processing device 120 may be local or remote. For example, the processing device 120 may access information and/or data stored in the scanner 110, the terminal device 140, and/or the storage device 130 via the network 150. As another example, the processing device 120 may be directly connected to the scanner 110, the terminal device 140, and/or the storage device 130 to access stored information and/or data. In some embodiments, the processing device 120 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 120 may be implemented by a computing device 200 having one or more components as illustrated in FIG. 2. In some embodiments, the processing device 120 may be implemented as a computing device 1412 having one or more components or devices as illustrated in FIG. 14.

The storage device 130 may store data, instructions, and/or any other information. In some embodiments, the storage device 130 may store data obtained from the scanner 110, the terminal device 140, and/or the processing device 120. In some embodiments, the storage device 130 may store data and/or instructions that the processing device 120 may execute or use to perform exemplary methods described in the present disclosure. In some embodiments, the storage device 130 may include a mass storage device, a removable storage device, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected to the network 150 to communicate with one or more other components (e.g., the processing device 120, the terminal device 140) of the imaging system 100. One or more components of the imaging system 100 may access the data or instructions stored in the storage device 130 via the network 150. In some embodiments, the storage device 130 may be directly connected to or communicate with one or more other components (e.g., the processing device 120, the terminal device 140) of the imaging system 100. In some embodiments, the storage device 130 may be part of the processing device 120.

The terminal device 140 may input/output signals, data, information, etc. In some embodiments, the terminal device 140 may enable a user interaction with the processing device 120. For example, the terminal device 140 may display an image of the subject on a screen 160. As another example, the terminal device 140 may obtain a user's input information through an input device (e.g., a keyboard, a touch screen, a brain wave monitoring device), and transmit the input information to the processing device 120 for further processing. The terminal device 140 may be a mobile device, a tablet computer, a laptop computer, a desktop computer, or the like, or any combination thereof. In some embodiments, the mobile device may include a home device, a wearable device, a virtual reality device, an augmented reality device, or the like, or any combination thereof. The home device may include a lighting device, a control device of an intelligent electrical apparatus, a monitoring device, a television, a video camera, an interphone, or the like, or any combination thereof. The wearable device may include a bracelet, a footgear, eyeglasses, a helmet, a watch, clothing, a backpack, an accessory, or the like, or any combination thereof. The virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal device 140 may be part of the processing device 120 or a peripheral device of the processing device 120 (e.g., a console connected to and/or communicating with the processing device 120).

The network 150 may include any suitable network that can facilitate the exchange of information and/or data for the imaging system 100. In some embodiments, one or more components (e.g., the scanner 110, the terminal device 140, the processing device 120, the storage device 130) of the imaging system 100 may communicate information and/or data with one or more other components of the imaging system 100 via the network 150. The network 150 may be and/or include a public network (e.g., the Internet), a private network (e.g., a local area network (LAN), a wide area network (WAN))), a wired network (e.g., an Ethernet network), a wireless network (e.g., an 802.11 network, a Wi-Fi network), a cellular network (e.g., a Long Term Evolution (LTE) network, 4G network, 5G network), a frame relay network, a virtual private network (VPN), a satellite network, a telephone network, routers, hubs, switches, server computers, and/or any combination thereof. Merely by way of example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the imaging system 100 may be connected to the network 150 to exchange data and/or information.

For illustration purposes, a coordinate system 170 is provided in FIG. 1. The coordinate system 170 may be a Cartesian system including an X-axis, a Y-axis, and a Z-axis. The X-axis and the Y-axis shown in FIG. 1 may be horizontal and the Z-axis may be vertical. As illustrated, the positive X direction along the X-axis may be from the left side to the right side of the table 114 viewed from the direction facing the front of the scanner 110; the positive Y direction along the Y-axis shown in FIG. 1 may be from the end to the head of the table 114; the positive Z direction along the Z-axis shown in FIG. 1 may be from the lower part to the upper part of the scanner 110.

It should be noted that the above description regarding the imaging system 100 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the imaging system 100 may include one or more additional components and/or one or more components of the imaging system 100 described above may be omitted. In some embodiments, a component of the imaging system 100 may be implemented on two or more sub-components. Two or more components of the imaging system 100 may be integrated into a single component.

FIG. 2 is a schematic diagram illustrating exemplary hardware and/or software components of an exemplary computing device according to some embodiments of the present disclosure. The computing device 200 may be configured to implement any component of the imaging system 100. For example, the scanner 110, the processing device 120, the storage device 130, and/or the terminal device 140 may be implemented on the computing device 200. Although only one such computing device is shown for convenience, the computer functions relating to the imaging system 100 as described herein may be implemented in a distributed fashion on a number of similar platforms, to distribute the processing load. As illustrated in FIG. 2, the computing device 200 may include a processor 210, a storage device 220, an input/output (I/O) 230, and a communication port 240.

The processor 210 may execute computer instructions (e.g., program codes) and perform functions of the processing device 120 in accordance with techniques described herein. The computer instructions may include, for example, routines, programs, objects, components, signals, data structures, procedures, modules, and functions, which perform particular functions described herein. In some embodiments, the processor 210 may perform instructions obtained from the terminal device 140 and/or the storage device 130. In some embodiments, the processor 210 may include one or more hardware processors, such as a microcontroller, a microprocessor, a reduced instruction set computer (RISC), an application-specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field-programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage device 220 may store data/information obtained from the scanner 110, the terminal device 140, the storage device 130, or any other component of the imaging system 100. In some embodiments, the storage device 220 may include a mass storage device, a removable storage device, a volatile read-and-write memory, a read-only memory (ROM), or the like, or any combination thereof. In some embodiments, the storage device 220 may store one or more programs and/or instructions to perform exemplary methods described in the present disclosure.

The I/O 230 may input or output signals, data, and/or information. In some embodiments, the I/O 230 may enable user interaction with the processing device 120. In some embodiments, the I/O 230 may include an input device and an output device. Exemplary input devices may include a keyboard, a mouse, a touch screen, a microphone, a camera capturing gestures, or the like, or a combination thereof. Exemplary output devices may include a display device, a loudspeaker, a printer, a projector, a 3D hologram, a light, a warning light, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected with a network (e.g., the network 150) to facilitate data communications. The communication port 240 may establish connections between the processing device 120 and the scanner 110, the terminal device 140, or the storage device 130. The connection may be a wired connection, a wireless connection, or a combination of both that enables data transmission and reception. The wired connection may include an electrical cable, an optical cable, a telephone wire, or the like, or any combination thereof. The wireless connection may include a Bluetooth network, a Wi-Fi network, a WiMax network, a WLAN, a ZigBee network, a mobile network (e.g., 3G, 4G, 5G), or the like, or any combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
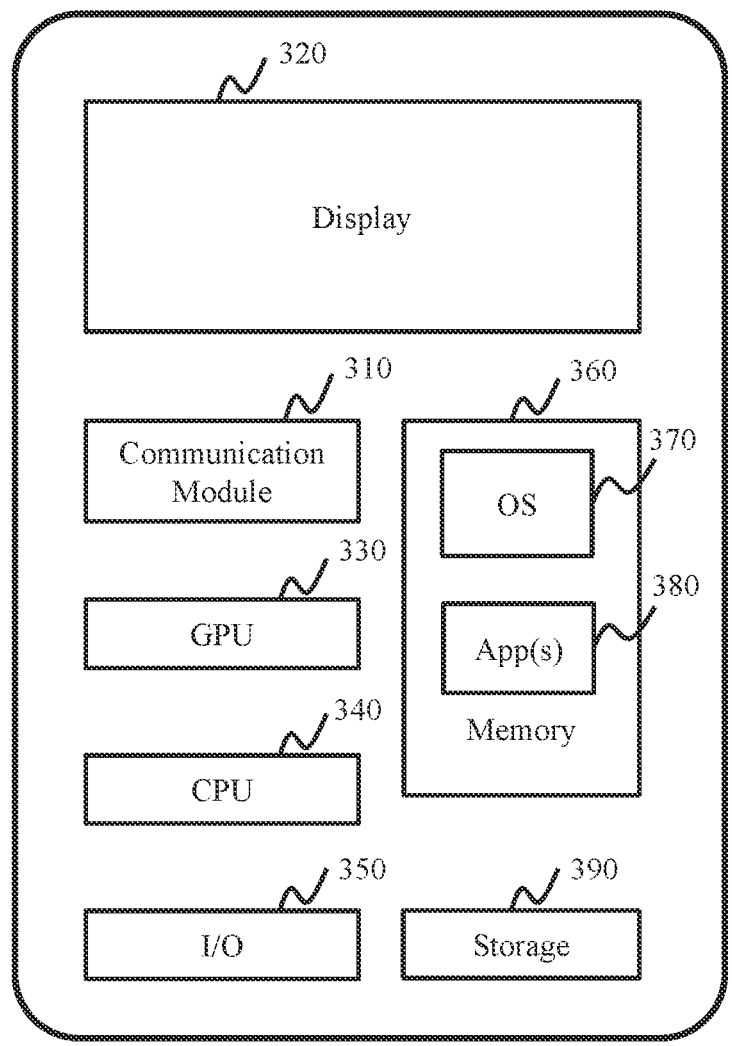
FIG. 3 is a block diagram illustrating exemplary hardware and/or software components of an exemplary requestor terminal according to some embodiments of the present disclosure.

FIG. 3 is a schematic diagram illustrating exemplary hardware and/or software components of an exemplary mobile device according to some embodiments of the present disclosure. In some embodiments, the processing device 120 or the terminal device 140 may be implemented on the mobile device 300. As illustrated in FIG. 3, the mobile device 300 may include a communication module 310, a display 320, a graphics processing unit (GPU) 330, a central processing unit (CPU) 340, an I/O 350, a memory 360, and storage 390. The CPU 340 may include interface circuits and processing circuits similar to the processor 210. In some embodiments, any other suitable component, including but not limited to a system bus or a controller (not shown), may also be included in the mobile device 300. In some embodiments, a mobile operating system 370 (e.g., iOS™, Android™, Windows Phone™) and one or more applications 380 may be loaded into the memory 360 from the storage 390 in order to be executed by the CPU 340. The applications 380 may include a browser or any other suitable mobile apps for receiving and rendering information relating to imaging from the imaging system on the mobile device 300. User interactions with the information stream may be achieved via the I/O devices 350 and provided to the processing device 120 and/or other components of the imaging system 100 via the network 150.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
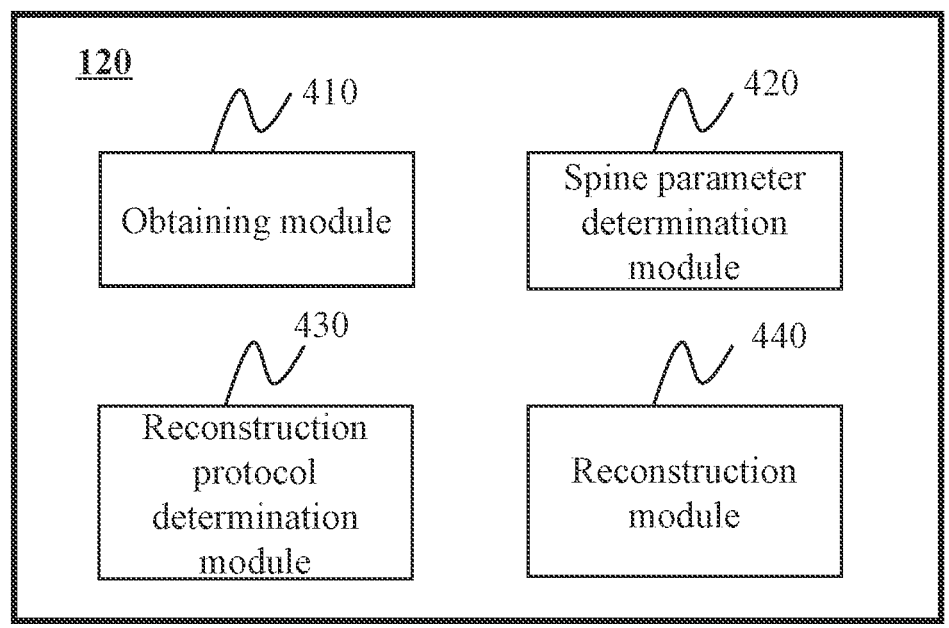
FIG. 4 is a block diagram illustrating an exemplary processing device according to some embodiments of the present disclosure.

FIG. 4 is a block diagram illustrating an exemplary processing device according to some embodiments of the present disclosure. As illustrated in FIG. 4, the processing device 120 may include an obtaining module 410, a spine parameter determination module 420, a reconstruction protocol determination module 430, and a reconstruction module 440.

The obtaining module 410 may obtain data or information. The obtaining module 410 may obtain data and/or information from the scanner 110, the storage device 130, the terminal(s) 140, or any devices or components capable of storing data via the network 150. In some embodiments, the obtaining module 410 may obtain scanning data of a spine of a subject.

The scanning data may be generated in an imaging scan performed on the subject by an imaging device (e.g., the scanner 110). In some embodiments, the imaging scan may correspond to a region, which includes the spine of the subject. In some embodiments, the imaging scan may be performed according to a scanning protocol. The scanning protocol may include parameters of the scanner 110, a scanning mode of the scanner 110, a size of the region, position information of the region, etc. During the imaging scan, the detector 112 may detect rays impinging thereon. The detected rays may include those passing through the spine of the subject. CT data of the spine of the subject may be generated based on the detected rays passing through the spine of the subject. In some embodiments, the CT data may be determined as the scanning data.

In some embodiments, a plurality of CT images of the spine of the subject may be reconstructed based on the CT data according to an image reconstruction algorithm. Exemplary image reconstruction algorithms may include an iterative reconstruction algorithm (e.g., a statistical reconstruction algorithm), a Fourier slice theorem algorithm, a filtered back projection (FBP) algorithm, a fan-beam reconstruction algorithm, an analytic reconstruction algorithm, or the like, or any combination thereof. Exemplary iterative reconstruction algorithms may include but not limited to a model-based iterative CT image reconstruction (MBIR), an algebraic reconstruction, a statistical reconstruction, a learned iterative reconstruction, etc. In some embodiments, the plurality of CT images may also be determined as the scanning data.

In some embodiments, the obtained data and/or information may further include processed results, user instructions, algorithms, parameters (e.g., scanning parameters of the scanner 110), program codes, information of one or more subject, or the like, or a combination thereof.

The spine parameter determination module 420 may determine centrum parameters or intervertebral disc parameters of the spine. The spine parameter determination module 420 determine the centrum parameters of each of a plurality of centrums of the spine based on the scanning data. In some embodiments, the centrum parameters of each centrum may include a label, a center point, a shape, a size, etc., of the centrum. The intervertebral disc parameters of an intervertebral disc may include a label, a range, a center point, at least two directions that define a plane of the intervertebral disc, an area, etc., of the intervertebral disc. The spine parameter determination module 420 may identify centrums and intervertebral discs in images of the spine of the subject, and determine the centrum parameters or intervertebral disc parameters of the spine.

The reconstruction protocol determination module 430 may determine an intervertebral disc reconstruction protocol for each of the at least one intervertebral disc. As used herein, an intervertebral disc reconstruction protocol of an intervertebral disc may refer to settings or parameters for reconstructing an image of the intervertebral disc. For each of the at least one intervertebral disc, the intervertebral disc reconstruction protocol may relate to image reconstruction parameters and one or more intervertebral disc parameters of the intervertebral disc. The image reconstruction parameters may refer to predetermined settings used in the reconstruction of images of the intervertebral disc. In some embodiments, the image reconstruction parameters may include a slice count, a slice thickness, a reconstruction dimension, etc.

The reconstruction module 440 may reconstruct images of an intervertebral disc. In some embodiments, the reconstruction module 440 may reconstruct images of an intervertebral disc (e.g., a target intervertebral disc) based on an intervertebral disc reconstruction protocol of the intervertebral disc. The intervertebral disc reconstruction protocol of the intervertebral disc may define the label, the range, the center point, or the at least two directions of the intervertebral disc, a slice thickness, a slice count, a reconstruction dimension, or the like, or a combination thereof. According to the intervertebral disc reconstruction protocol of the intervertebral disc, the reconstruction planes of the intervertebral disc may coincide with or parallel to the plane of the intervertebral disc.

The modules in the processing device 120 may be connected to or communicated with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. Two or more of the modules may be combined into a single module, and any one of the modules may be divided into two or more units. For example, the above-mentioned modules may be integrated into a console (not shown). Via the console, a user may set parameters for scanning a subject, controlling imaging processes, adjusting reconstruction protocols for reconstruction of an image, viewing images, etc. As another example, the processing device 120 may include a storage module (not shown) configured to store information and/or data (e.g., scanning data, images) associated with the above-mentioned modules.

Figure 5:
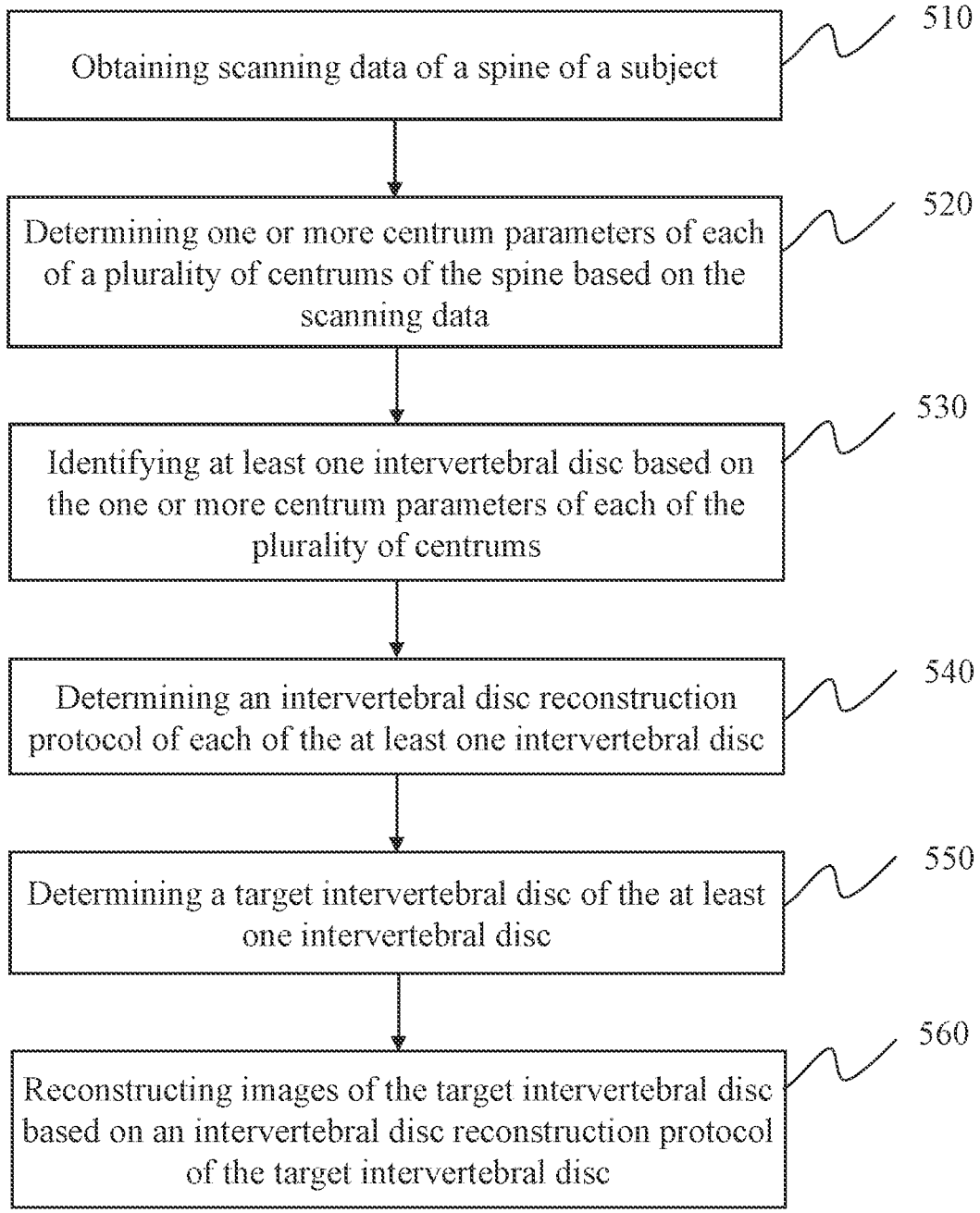
FIG. 5 is a flowchart illustrating an exemplary process for reconstructing an image of a target intervertebral disc according to some embodiments of the present disclosure.

FIG. 5 is a flowchart illustrating an exemplary process for reconstructing an image of a target intervertebral disc according to some embodiments of the present disclosure. In some embodiments, the process 500 may be executed by the imaging system 100. For example, the process 500 may be implemented as a set of instructions (e.g., an application) stored in a storage device (e.g., the storage device 130). The modules described in FIG. 4 and/or the processor 210 may execute the set of instructions and may accordingly be directed to perform the process 500. The operations of the illustrated process presented below are intended to be illustrative. In some embodiments, the process 500 may be accomplished with one or more additional operations not described and/or without one or more of the operations discussed. Additionally, the order of the operations of process 500 illustrated in FIG. 5 and described below is not intended to be limiting.

In 510, the processing device 120 (e.g., the obtaining module 410 or the processor 210) may obtain scanning data of a spine of a subject.

The subject may include a biological subject and/or a non-biological subject. The biological subject may be a human being, an animal, a plant, or a specific portion, organ, and/or tissue thereof. For example, the subject may include a spine of a human being or an animal, or a portion thereof. In some embodiments, the subject may be a man-made composition of organic and/or inorganic matters that are with or without life. For example, the subject may include a phantom of a spine of a human being or an animal, or a portion thereof.

The scanning data may be generated in an imaging scan performed on the subject by an imaging device (e.g., the scanner 110). In some embodiments, the imaging scan may correspond to a region, which includes the spine of the subject. In some embodiments, the imaging scan may be performed according to a scanning protocol. The scanning protocol may include parameters of the scanner 110, a scanning mode of the scanner 110, a size of the region, position information of the region, etc. During the imaging scan, the detector 112 may detect rays impinging thereon. The detected rays may include those passing through the spine of the subject. CT data of the spine of the subject may be generated based on the detected rays passing through the spine of the subject. In some embodiments, the CT data may be determined as the scanning data.

In some embodiments, a plurality of CT images of the spine of the subject may be reconstructed based on the CT data according to an image reconstruction algorithm. Exemplary image reconstruction algorithms may include an iterative reconstruction algorithm (e.g., a statistical reconstruction algorithm), a Fourier slice theorem algorithm, a filtered back projection (FBP) algorithm, a fan-beam reconstruction algorithm, an analytic reconstruction algorithm, or the like, or any combination thereof. Exemplary iterative reconstruction algorithms may include but not limited to a model-based iterative CT image reconstruction (MBIR), an algebraic reconstruction, a statistical reconstruction, a learned iterative reconstruction, etc.

In some embodiments, each of the plurality of CT images may be a two-dimensional (2D) image or 2D image data. For example, the plurality of CT images may be 2D images (also referred to as slices). The slices may be arranged in a predetermined sequence. In some embodiments, the slices may include transverse images arranged along a direction from the superior to the inferior of a patient, or vice versa. In some embodiments, the slices may include sagittal images arranged along the direction from the left to the right of the patient, or vice versa. In some embodiments, the slices may include coronal images arranged along the direction from the posterior to the anterior of the patient, or vice versa. In some embodiments, the plurality of CT images arranged in the predetermined sequence may be transmitted, in accordance with to a designated component of the processing device 120 (e.g., the spine parameter determination module 420) or a work station (not shown) so as to obtain different views of the spine of the subject. The different views may include, e.g., a coronal view, a sagittal view, and/or a transverse view. In some embodiments, the plurality of CT images may constitute a three-dimensional (3D) image or 3D image data of the spine of the subject. In some embodiments, the plurality of CT images may also be determined as the scanning data.

In 520, the processing device 120 (e.g., the spine parameter determination module 420 or the processor 210) may determine one or more centrum parameters of each of a plurality of centrums of the spine based on the scanning data. As used herein, the scanning data may include the data acquired by the scanner 110, or data in the image domain including, e.g., an image obtained by image reconstruction based on the data acquired by the scanner 110.

The spine of the subject may include a plurality of vertebrae. The plurality of vertebrae may be of various types, including, e.g., cervical vertebrae, thoracic vertebrae, lumbar vertebrae, sacral vertebrae, caudal vertebrae, etc. Merely by way of example, a spine of an adult may include seven cervical vertebrae, twelve thoracic vertebrae, five lumbar vertebrae, one sacral vertebra, and one caudal vertebra. Each of the plurality of vertebra may include a main body (also referred to as a centrum).

The processing device 120 may identify the plurality of centrums based on the scanning data of the spine. In some embodiments, the processing device 120 may identify the plurality of centrums using a centrum recognition algorithm. The centrum recognition algorithm may be used to recognize a centrum in an image based on anatomical features (e.g., an outline, a shape, a size, an edge, a gray value, or the like, or a combination thereof) of the centrum in the image. Exemplary centrum recognition algorithms may include a scale-invariant feature transform (SIFT) algorithm, a speed up robust feature (SURF) algorithm, a features from accelerated segment test (FAST) algorithm, a binary robust independent elementary features (BRIEF) algorithm, an oriented FAST and rotated BRIEF (ORB) algorithm, or the like, or a combination thereof.

After the plurality of centrums of the spine are determined, one or more centrum parameters of each of the plurality of centrums of the spine may be determined. The one or more centrum parameters of each of the plurality of centrums may be attributes of the centrum. In some embodiments, the one or more centrum parameters of each centrum may include a label, a center point, a shape, a size, etc., of the centrum. In some embodiments, the one or more centrum parameters of each of the plurality of centrums of the spine may be determined based on the scanning data of the spine of the subject.

Figure 6:
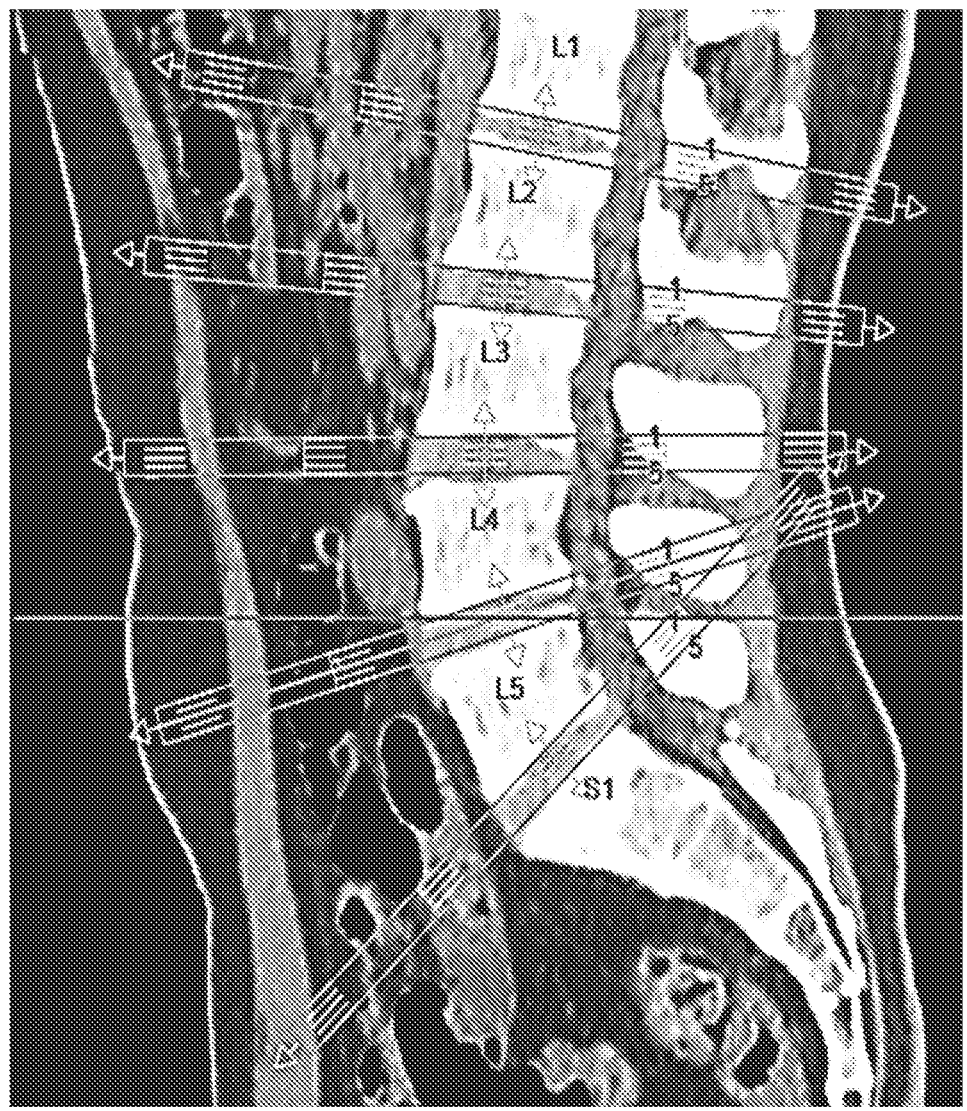
FIG. 6 illustrates a sagittal view of a portion of a spine of a subject according to some embodiments of the present disclosure.

A label of a centrum may be a representation of the centrum. In some embodiments, a label of a centrum may be determined by a user, according to default settings of the imaging system 100, etc. For example, a user may determine any suitable text or symbol as a label of a centrum. In some embodiments, a label of a centrum may be determined based on a type and/or a position of a corresponding vertebra. Illustrated in FIG. 6 is a sagittal view of a portion of a spine of a subject that includes multiple lumbar vertebrae and one sacral vertebra. Each of the multiple lumbar vertebrae may include a centrum. As shown in FIG. 6, the multiple lumbar vertebrae may include a first centrum, a second centrum, a third centrum, a fourth centrum, and a fifth centrum. The labels of centrums of the multiple lumbar vertebrae may be determined as L1, L2, L3, L4, and L5, respectively, along a direction from the superior to the inferior of the subject. Similarly, a label of a centrum of the sacral vertebrae may be determined as S1.

A center point of a centrum may be a geometric center point of the centrum. In some embodiments, a center point of a centrum may be represented by coordinates of the center point with reference to the coordinate system 170. In some embodiments, the coordinates of the center point may be determined based on coordinates of elements (e.g., pixels or voxels) of the centrum. Merely by way of example, the coordinates of the elements in one or more images (e.g., a 3D image, a 2D coronal image, a 2D sagittal image, and/or a 2D transverse image) of the centrum. A mean value of the coordinates of the elements of the centrum on each axis of the coordinate system 170 may be determined. Mean values of the coordinates of the elements on the axes of the coordinate system 170 may be determined as coordinates of the center point of the centrum.

In some embodiments, a centrum positioning model may be obtained. The processing device 120 may identify the plurality of centrums of the spine and/or determine the one or more centrum parameters of each of the plurality of centrums based on the centrum positioning model. Exemplary centrum positioning models may include a deep belief network (DBN), a Stacked Auto-Encoders (SAE), a logistic regression (LR) model, a support vector machine (SVM) model, a decision tree model, a Naive Bayesian Model, a random forest model, or a Restricted Boltzmann Machine (RBM), a Gradient Boosting Decision Tree (GBDT) model, a LambdaMART model, an adaptive boosting model, a recurrent neural network (RNN) model, a convolutional network model, a hidden Markov model, a perceptron neural network model, a Hopfield network model, or the like, or any combination thereof.

In some embodiments, the centrum positioning model may be a model trained based on sample data (e.g., a plurality of sample images). In some embodiments, the sample data may include historical CT images of spines of multiple subjects. In some embodiments, sample anatomical features and/or sample centrum parameters (e.g., sample labels, sample center points, etc.) of centrums of the spines in the sample data may be determined and used to train a preliminary centrum positioning model. The sample anatomical features and/or the sample centrum parameters may be in the form of a vector, a matrix, etc. The sample anatomical features and/or the sample centrum parameters may be input into the preliminary centrum positioning model, and the preliminary centrum positioning model may be iteratively updated until a condition is satisfied (e.g., a loss function reaching convergence). The updated centrum positioning model determined in a latest iteration may be designated as the centrum positioning model. The processing device 120 may identify the plurality of centrums of the spine and/or determine the one or more centrum parameters of each of the plurality of centrums by inputting the scanning data of the spine into the centrum positioning model.

In 530, the processing device 120 (e.g., the spine parameter determination module 420 or the processor 210) may identify at least one intervertebral disc based on the one or more centrum parameters of each of the plurality of centrums.

After the one or more centrum parameters of each of the plurality of centrums are determined, at least one intervertebral disc may be determined. Each of the at least one intervertebral disc may be located between a pair of neighboring centrums of the plurality of centrums. As used herein, any two centrums may be referred to as a pair of neighboring centrums if there are no other centrum located between the two centrums. In some embodiments, a region including a pair of neighboring centrums may be determined in one or more images of the spine of the subject. Merely by way of example, for a pair of neighboring centrums, the region may be determined based on center points of the pair of neighboring centrums in the one or more images of the spine. An intervertebral disc between the pair of neighboring centrums may be included in the region. In some embodiments, the intervertebral disc may be identified in the region by segmenting the region. Details regarding the identification of the at least one intervertebral disc can be found elsewhere in the present disclosure. See, for example, FIG. 7A and the descriptions thereof.

In 540, the processing device 120 (e.g., the reconstruction protocol determination module 430 or the processor 210) may determine an intervertebral disc reconstruction protocol for each of the at least one intervertebral disc.

As used herein, an intervertebral disc reconstruction protocol of an intervertebral disc may refer to settings or parameters for reconstructing an image of the intervertebral disc. For each of the at least one intervertebral disc, the intervertebral disc reconstruction protocol may relate to image reconstruction parameters and one or more intervertebral disc parameters of the intervertebral disc. The image reconstruction parameters may refer to predetermined settings used in the reconstruction of images of the intervertebral disc. In some embodiments, the image reconstruction parameters may include a slice count, a slice thickness, a reconstruction dimension, etc. The slice count may refer to a count (or number) of slices (i.e., reconstruction planes) of the intervertebral disc. The slice thickness may refer to a thickness of a slice. The reconstruction dimension may include two dimensions or three dimensions. In some embodiments, the image reconstruction parameters may be set by a user (e.g., a doctor or a technician), according to default settings of the imaging system 100, etc.

The one or more intervertebral disc parameters of an intervertebral disc may include attributes of the intervertebral disc. The one or more intervertebral disc parameters of the intervertebral disc may include a label, a range, a center point, at least two directions that define a plane of the intervertebral disc, an area, etc., of the intervertebral disc. The label of the intervertebral disc may be a representation of the intervertebral disc. In some embodiments, the label of the intervertebral disc may be determined based on labels of a pair of neighboring centrums between which the intervertebral disc is located. Merely by way of example, a label of an intervertebral disc between a pair of neighboring centrums labelled L4 and L5 may be determined as L4-L5. The range of the intervertebral disc may be a range of the intervertebral disc in a thickness direction of the intervertebral disc. The center point of the intervertebral disc refers to a geometric center point of the intervertebral disc. In some embodiments, the center point of the intervertebral disc may be represented by coordinates of the center point with reference to the coordinate system 170. In some embodiments, the coordinates of the center point may be determined based on coordinates of elements (e.g., pixels or voxels) of the intervertebral disc. The at least two directions of the intervertebral disc may form a plane or a set of parallel planes where the intervertebral disc is located (also referred to as the plane of the intervertebral disc). In some embodiments, the at least two directions may be any directions on the plane. In some embodiments, the at least two directions may be intersecting with each other. In combination with the slice thickness and/or the slice count, the at least two directions and the range of the intervertebral disc may define the reconstruction planes of the intervertebral disc.

Referring to FIG. 6, directions and ranges of intervertebral discs are represented using the rectangular boxes. As for a rectangular box of an intervertebral disc, the length direction of the rectangular box may represent the direction of the intervertebral disc in the sagittal view of the portion of the spine; the width direction of the rectangular box may represent the range of the intervertebral disc. In some embodiments, the processing device 120 may obtain coordinates of elements (e.g., pixels or voxels) of the intervertebral disc. As shown in FIG. 6, the directions of the intervertebral discs in the sagittal view of the portion of the spine may be unparallel to each other.

The range, the center point, and/or the at least two directions of the intervertebral disc may be determined based on the coordinates of the elements of the intervertebral disc. Details regarding the determination of the intervertebral disc reconstruction protocol of each of the at least one intervertebral disc can be found elsewhere in the present disclosure. See, for example, FIG. 7B and the descriptions thereof. The processing device 120 may reconstruct images of an intervertebral disc based on the intervertebral disc reconstruction protocol of the intervertebral disc.

In some embodiments, since the directions of the intervertebral discs are unparallel to each other, images of different intervertebral discs may be reconstructed in multiple planes in a three-dimensional space. In some embodiments, the intervertebral disc reconstruction protocol of each of the at least one intervertebral disc may relate to the multi-planar reconstruction (MPR) technique. For instance, reconstruction planes of the different intervertebral discs may be parallel to corresponding planes on which the different intervertebral discs are located, respectively. The image reconstruction of an intervertebral disc may be conducted according to the intervertebral disc reconstruction protocol of the intervertebral disc. Reconstructed images of the intervertebral disc may provide an optimal view of the intervertebral disc, and enable a better observation of the intervertebral disc.

In 550, the processing device 120 (e.g., the reconstruction module 440 or the processor 210) may determine a target intervertebral disc of the at least one intervertebral disc.

The target intervertebral disc may be a specific intervertebral disc among the at least one intervertebral disc. The target intervertebral disc may be specified by a user, according to default settings of the imaging system 100, etc. In some embodiments, the target intervertebral disc may be determined based on an instruction from a user. For example, an image of the spine of the subject (e.g., a CT image obtained in 510) including at least one intervertebral disc may be displayed to a user via an interface of a terminal device (e.g., the terminal device 140). The user may select any intervertebral disc from the at least one intervertebral disc according to actual situations. If the user chooses to view an image of a target intervertebral disc (e.g., the intervertebral disc L4-L5), the user may input a label of the target intervertebral disc or select the target intervertebral disc on the interface manually. The processing device 120 may determine the target intervertebral disc based on the input or the selection operation of the user in the interface.

In some embodiments, the target intervertebral disc may be determined by the imaging system 100 automatically. For example, the processing device 120 may extract anatomical features (e.g., a size, a shape, a density, etc.) of a least a part of the at least one intervertebral disc, and identify lesions on the at least one intervertebral disc based on the morphological features. An intervertebral discs with a lesion thereon may be of interest to a user (e.g., for diagnosis and/or treatment purposes) and therefore designated as the target intervertebral disc.

In 560, the processing device 120 (e.g., the reconstruction module 440 or the processor 210) may reconstruct images of the target intervertebral disc based on an intervertebral disc reconstruction protocol of the target intervertebral disc.

The processing device 120 may reconstruct the images of the target intervertebral disc based on the intervertebral disc reconstruction protocol of the target intervertebral disc. The intervertebral disc reconstruction protocol of the target intervertebral disc may define the label, the range, the center point, or the at least two directions of the intervertebral disc, a slice thickness, a slice count, a reconstruction dimension, or the like, or a combination thereof. According to the intervertebral disc reconstruction protocol of the target intervertebral disc, the reconstruction planes of the target intervertebral disc may coincide with or parallel to the plane of the target intervertebral disc.

In some embodiments, the processing device 120 may further transmit the one or more reconstructed images of the target intervertebral disc to the terminal device 140. The terminal device 140 may include a display device (e.g., an LCD, a light-emitting diode (LED)-based display, a flat panel display, a curved screen, an immersive virtual reality display) for displaying the one or more reconstructed images of the target intervertebral disc. A user (e.g., a doctor) may view the one or more reconstructed images of the target intervertebral disc displayed on the display device and input diagnosis information regarding the target intervertebral disc via the terminal device 140. The diagnosis information may include basic information (e.g., the age, the gender, etc.) of the subject, a detailed description regarding the target intervertebral disc, a suspected lesion of the target intervertebral disc, a recommended treatment scheme, etc. In some embodiments, the diagnosis information may be in the form of text, an audio segment, a video clip, etc. The processing device 120 may receive the diagnosis information from the terminal device 140. The processing device 120 may generate a report regarding the target intervertebral disc based on the diagnosis information and the reconstructed images of the target intervertebral disc. The report may be in the form of an electronic file. In some embodiments, the processing device 120 may also send the report to a printer for printing, to a terminal device 140 for display, and/or to a storage device for storage.

According to some embodiments of the present disclosure, the intervertebral disc reconstruction protocol of each of the at least one intervertebral disc may be determined automatically. For each of the at least one intervertebral disc, the intervertebral disc reconstruction protocol may relate to one or more parameters (e.g., a range, a center point, at least two directions, etc.) of the intervertebral disc. In this case, the plane and the range of the vertebral disc may be determined. Images of the intervertebral disc may be reconstructed with respect to the plane in the range according to the MPR technique. Thus, the imaging of the intervertebral disc of the spine may be fulfilled accurately and efficiently.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the at least one intervertebral disc may be identified based on the scanning data obtained in 510 or an image reconstructed based on the scanning data. Merely for illustration, an image segmentation algorithm or an intervertebral disc segmentation model may be used to identify the at least one intervertebral disc. Exemplary image segmentation algorithms may include a threshold-based segmentation algorithm, an edge-based segmentation algorithm, a region-based segmentation algorithm, a graph theory-based segmentation algorithm, an energy functional-based segmentation algorithm, a wavelet-based segmentation algorithm, a neural network-based segmentation algorithm, etc. Exemplary intervertebral disc segmentation models may include a deep belief network (DBN), a Stacked Auto-Encoders (SAE), a logistic regression (LR) model, a support vector machine (SVM) model, a decision tree model, a Naive Bayesian Model, a random forest model, or a Restricted Boltzmann Machine (RBM), a Gradient Boosting Decision Tree (GBDT) model, a LambdaMART model, an adaptive boosting model, a recurrent neural network (RNN) model, a convolutional network model, a hidden Markov model, a perceptron neural network model, a Hopfield network model, or the like, or any combination thereof. As another example, the one or more centrum parameters of each of a plurality of centrums of the spine determined in 520 may only include a label of each of the plurality of centrums of the spine. The processing device 120 may identify the at least one intervertebral disc based on the label of each of the plurality of centrums of the spine and/or the scanning data obtained in 510 or an image reconstructed based on the scanning data.

FIG. 7A is a flowchart illustrating an exemplary process for identify at least one intervertebral disc and determining an intervertebral disc reconstruction protocol of each of the at least one intervertebral disc according to some embodiments of the present disclosure. In some embodiments, the process 700 may be executed by the imaging system 100. For example, the process 700 may be implemented as a set of instructions (e.g., an application) stored in a storage device (e.g., the storage device 130). The modules described in FIG. 4 and/or the processor 210 may execute the set of instructions and may accordingly be directed to perform the process 700. The operations of the illustrated process presented below are intended to be illustrative. In some embodiments, the process 700 may be accomplished with one or more additional operations not described and/or without one or more of the operations discussed. Additionally, the order of the operations of process 700 illustrated in FIG. 7A and described below is not intended to be limiting. In some embodiments, the operation 530 of the process 500 as illustrated in FIG. 5 may be performed according to the process 700.

In 710, the processing device 120 (e.g., the spine parameter determination module 420 or the processor 210) may determine at least one region in one or more images of the spine, each of the at least one region including an intervertebral disc.

In order to identify an intervertebral disc, a region that includes the intervertebral disc may be determined in each of the one or more images (e.g., CT images) of the spine. The region may have a shape of a rectangle, a triangle, a circle, etc. In some embodiments, the region may be determined based on center points of a pair of neighboring centrums. The intervertebral disc may be located between the pair of neighboring centrums. In some embodiments, at least one of the center points of the pair of neighboring centrums may be within the region. In some embodiments, at least one of the center points of the pair of neighboring centrums may be on a boundary of the region.

Each of FIGS. 8A and 8B shows a sagittal view of a portion of the spine of a subject. As shown in FIG. 8A, the portion of the spine may include centrums L1 through L5 and S1. Center points of the centrums L1 through L5 and S1 may be determined and represented by black dots in the sagittal view. The centrums L1 through L5 and S1 may constitute five pairs of neighboring centrums. An intervertebral disc may be located between each pair of the five pairs of neighboring centrums.

An intervertebral disc L4-L5, which is between the centrums L4 and L5, is taken as an example. As shown in FIG.

8B, a region 810 including the intervertebral disc L4-L5 may be determined. The region 810 may be a rectangle denoted by a dashed box. The region 810 may be determined based on the center points of the pair of neighboring centrums L4 and L5. The center points of the pair of neighboring centrums L4 and L5 may be on two opposite sides of the dashed box.

In 720, the processing device 120 (e.g., the spine parameter determination module 420 or the processor 210) may identify an intervertebral disc from each of the at least one region.

In some embodiments, the processing device 120 may identify an intervertebral disc between a pair of neighboring centrums by segmenting each of the at least one region in each of the one or more images including the pair of neighboring centrums. In some embodiments, the at least one region in the one or more images may be segmented using an image segmentation algorithm. Exemplary image segmentation algorithms may include a threshold-based segmentation algorithm, an edge-based segmentation algorithm, a region-based segmentation algorithm, a graph theory-based segmentation algorithm, an energy functional-based segmentation algorithm, a wavelet-based segmentation algorithm, a neural network-based segmentation algorithm, etc.

In some embodiments, an intervertebral disc segmentation model may be obtained. The processing device 120 may identify an intervertebral disc from each of the at least one region based on the intervertebral disc segmentation model. Exemplary intervertebral disc segmentation models may include a deep belief network (DBN), a Stacked Auto-Encoders (SAE), a logistic regression (LR) model, a support vector machine (SVM) model, a decision tree model, a Naive Bayesian Model, a random forest model, or a Restricted Boltzmann Machine (RBM), a Gradient Boosting Decision Tree (GBDT) model, a LambdaMART model, an adaptive boosting model, a recurrent neural network (RNN) model, a convolutional network model, a hidden Markov model, a perceptron neural network model, a Hopfield network model, or the like, or any combination thereof.

In some embodiments, the intervertebral disc segmentation model may be a model trained based on a plurality of sample images. In some embodiments, the plurality of sample images may include historical CT images of spines of multiple subjects. In some embodiments, sample anatomical features of intervertebral discs of the spines in the plurality of sample images may be determined and used to train a preliminary intervertebral disc segmentation model. The sample anatomical features may be input into the preliminary intervertebral disc segmentation model, and the preliminary intervertebral disc segmentation model may be iteratively updated until a condition is satisfied (e.g., a loss function reaches a convergence). The updated intervertebral disc segmentation model in a latest iteration may be designated as the intervertebral disc segmentation model. In some embodiments, at least a part of the one or more images may include at least one region. The processing device 120 may identify an intervertebral disc in each region of the at least one region of the one or more images by inputting the each region into the intervertebral disc segmentation model. An exemplary intervertebral disc 820 identified by segmenting a region that accommodates the intervertebral disc is illustrated in FIG. 8C. In some embodiments, the processing device 120 may identify the intervertebral disc 820 by analyzing the region 810 in the sagittal view using the intervertebral disc segmentation model.

FIG. 7B is a flowchart illustrating an exemplary process for determining an intervertebral disc reconstruction protocol of each of the at least one intervertebral disc according to some embodiments of the present disclosure. In some embodiments, the process 750 may be executed by the imaging system 100. For example, the process 750 may be implemented as a set of instructions (e.g., an application) stored in a storage device (e.g., the storage device 130). The modules described in FIG. 4 and/or the processor 210 may execute the set of instructions and may accordingly be directed to perform the process 750. The operations of the illustrated process presented below are intended to be illustrative. In some embodiments, the process 750 may be accomplished with one or more additional operations not described and/or without one or more of the operations discussed. Additionally, the order of the operations of process 750 illustrated in FIG. 7B and described below is not intended to be limiting. In some embodiments, the operation 540 of the process 500 as illustrated in FIG. 5 may be performed according to the process 750.

In 760, the processing device 120 (e.g., the reconstruction protocol determination module 430 or the processor 210) may determine one or more intervertebral disc parameters of each of the at least one intervertebral disc.

In some embodiments, the one or more intervertebral disc parameters of each of the at least one intervertebral disc may include a label, a range, a center point, at least two directions, an area, etc., of the intervertebral disc. In some embodiments, the processing device 120 may obtain coordinates of elements (e.g., pixels or voxels) of the intervertebral disc. The range, the center point, and/or the at least two directions of the intervertebral disc may be determined based on the coordinates of the elements of the intervertebral disc. In this case, a plane and the range of the vertebral disc may be determined.

In some embodiments, the at least two directions of each of the at least one intervertebral disc may be determined according to a principle component analysis (PCA) approach. The PCA approach may be used to determine at least two characteristic directions of each of the at least one intervertebral disc. The at least two characteristic directions may relate to a shape of the intervertebral disc. The at least two characteristic directions may be perpendicular to each other. Assuming that an intervertebral disc is an oval disc (e.g., the intervertebral disc has a shape of an oval in a cross section perpendicular to a thickness direction of the intervertebral disc), the at least two characteristic directions of the intervertebral disc may include at least a major axis and a minor axis of the oval. The at least two characteristic directions may be determined as the at least two directions of each of the at least one intervertebral disc (also referred to as main directions).

Figure 9:
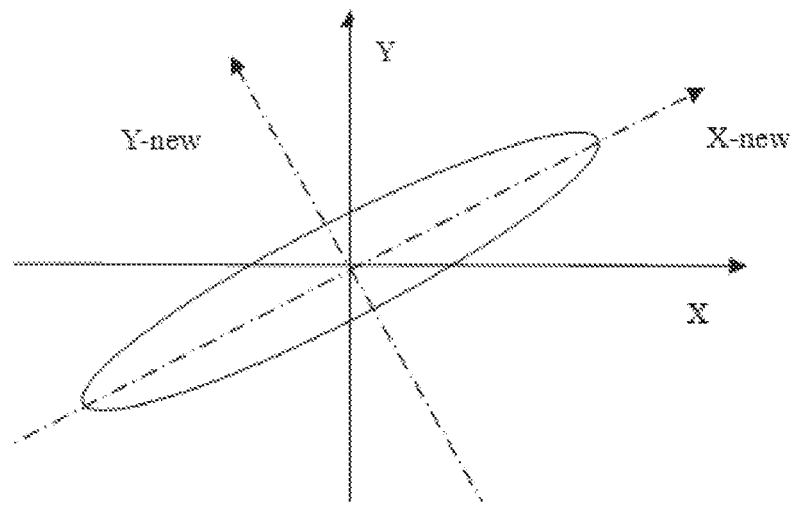
FIG. 9 illustrates exemplary directions of a 2D intervertebral disc according to some embodiments of the present disclosure.

FIG. 9 illustrates exemplary directions of a 2D intervertebral disc according to some embodiments of the present disclosure. As shown in FIG. 9, the 2D intervertebral disc may be in the X-Y plane of the coordinate system 170. Two characteristic directions of the intervertebral disc may be determined according to the PCA approach. The two characteristic directions of the intervertebral disc may include an X-new direction and a Y-new direction. The 2D intervertebral disc has the shape of an oval. The X-new direction and the Y-new direction may be along a major axis and a minor axis of the oval, respectively. The X-new direction and the Y-new direction may be perpendicular to each other. The X-new direction and the Y-new direction may be determined as the at least two directions of the 2D intervertebral disc.

Figure 10:
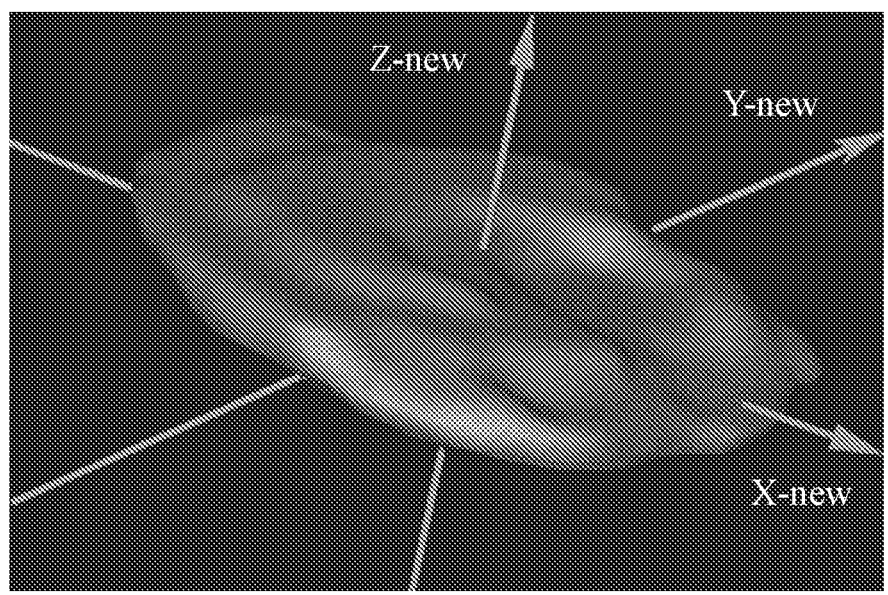
FIG. 10 illustrates exemplary directions of a 3D intervertebral disc according to some embodiments of the present disclosure.

FIG. 10 illustrates exemplary directions of a 3D intervertebral disc according to some embodiments of the present disclosure. Three characteristic directions of the 3D intervertebral disc may be determined according to the PCA approach. The three characteristic directions of the intervertebral disc may include an X-new direction, a Y-new direction, and a Z-new direction. The 3D intervertebral disc be an oval disc. The Z-new direction may be a thickness direction of the 3D intervertebral disc. The X-new direction and the Y-new direction may be along a major axis and a minor axis of an oval cross section of the 3D intervertebral disc, respectively. The oval cross section of the 3D intervertebral disc may be perpendicular to the thickness direction. The X-new direction, the Y-new direction, and the Z-new direction may be perpendicular to each other. The X-new direction, the Y-new direction, and the Z-new direction may be determined as the at least two directions of the 3D intervertebral disc.

In 770, the processing device 120 (e.g., the reconstruction protocol determination module 430) may determine an intervertebral disc reconstruction protocol of each of the at least one intervertebral disc based on image reconstruction parameters and the one or more intervertebral disc parameters of the each intervertebral disc.

In some embodiments, for each of the at least one intervertebral disc, the intervertebral disc reconstruction protocol may be determined based on image reconstruction parameters and the one or more intervertebral disc parameters of each intervertebral disc. In some embodiments, the image reconstruction parameters may include a slice count, a slice thickness, a reconstruction dimension, etc.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the intervertebral disc reconstruction protocol of each of the at least one intervertebral disc may also be determined based on a reconstruction protocol determination model. The reconstruction protocol determination model may include a deep belief network (DBN), a Stacked Auto-Encoders (SAE), a logistic regression (LR) model, a support vector machine (SVM) model, a decision tree model, a Naive Bayesian Model, a random forest model, or a Restricted Boltzmann Machine (RBM), a Gradient Boosting Decision Tree (GBDT) model, a LambdaMART model, an adaptive boosting model, a recurrent neural network (RNN) model, a convolutional network model, a hidden Markov model, a perceptron neural network model, a Hopfield network model, or the like, or any combination thereof.

Figure 11A:
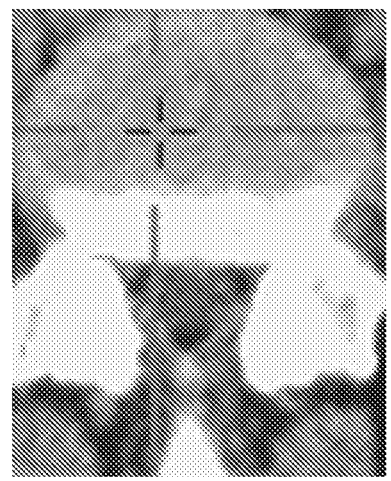
FIG. 11A illustrates an image of an intervertebral disc in a transverse view according to some embodiments of the present disclosure.
Figure 11B:
FIG. 11B illustrates an image of the intervertebral disc reconstructed based on an intervertebral disc reconstruction protocol of the intervertebral disc using an MPR technique.

It is understood that the reconstruction of images of an intervertebral disc may be carried out along the thickness direction of the intervertebral disc based on an intervertebral disc reconstruction protocol of the intervertebral disc. The thickness direction may be, for example, the Y-new direction in FIG. 9 or the Z-new direction in FIG. 10. The images of the intervertebral disc may be reconstructed within a range of the intervertebral disc. FIG. 11A illustrates an image of an intervertebral disc in a transverse view according to some embodiments of the present disclosure. Merely by way of example, the intervertebral disc may be an intervertebral disc L4-L5. The image of the intervertebral disc in the transverse view may be perpendicular to the Y axis of the coordinate system 170. Since the plane of the intervertebral disc is unparallel to the reconstruction planes (e.g., planes parallel to the X-Z plane of the coordinate system 170), the image shown in FIG. 11A includes a portion of the intervertebral disc at an upper part of the image and a portion of a neighboring centrum of the intervertebral disc at a lower part of the image. FIG. 11B illustrates an image of the intervertebral disc reconstructed based on an intervertebral disc reconstruction protocol of the intervertebral disc using an MPR technique. The reconstruction planes may coincide with or parallel to the plane of the intervertebral disc. As shown in FIG. 11B, the entire intervertebral disc is reconstructed and presented in the image.

Figure 12A:
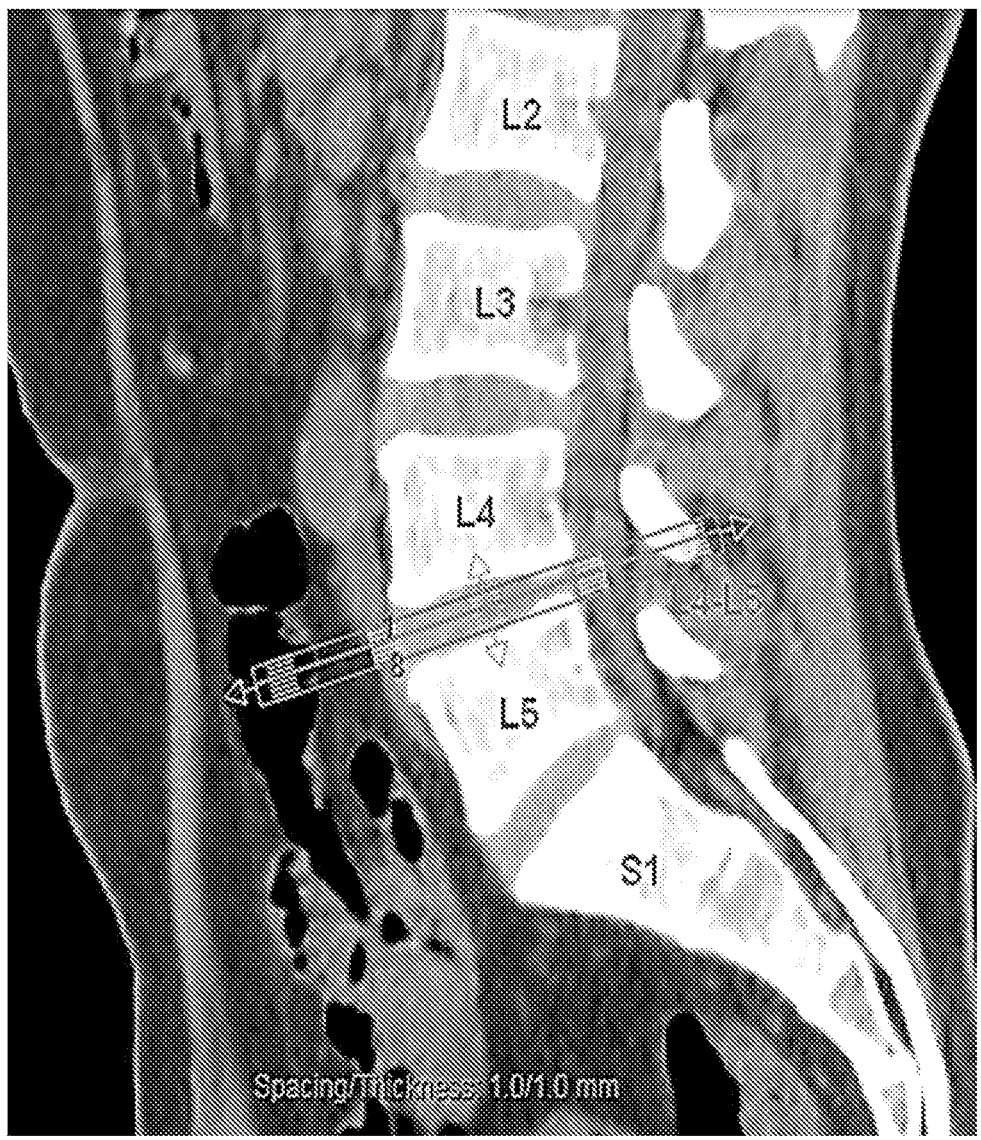
FIGS. 12A and 12B illustrate a sagittal view and a coronal view of a spine of a subject, respectively, according to some embodiments of the present disclosure.
Figure 12B:

In some embodiments, the intervertebral disc reconstruction protocol of each of the at least one intervertebral disc may be determined based on 2D images (e.g., a coronal view or a sagittal view) of the spine of the subject. The reconstruction planes shown in different 2D images may be presented independently of each other. Merely for illustration purposes, FIGS. 12A and 12B illustrate a sagittal view and a coronal view of a spine of a subject, respectively. Reconstruction planes of an intervertebral disc L4-L5 is determined and illustrated by means of rectangular boxes in the sagittal view and the coronal view. Length directions of the rectangular boxes may represent directions of the intervertebral disc L4-L5. Width directions of the rectangular boxes may represent ranges of the intervertebral disc L4-L5. The direction of the intervertebral disc L4-L5 in the sagittal view denoted by the double arrow in FIG. 12A may be perpendicular to the direction of the intervertebral disc L4-L5 in the coronal view denoted by the double arrow in FIG. 12B. Thus, the direction of the intervertebral disc L4-L5 in the sagittal view may be different from the direction of the intervertebral disc L4-L5 in the coronal view. If the reconstruction planes of the intervertebral disc L4-L5 are updated (e.g., tilted), the directions of the intervertebral disc L4-L5 in the sagittal view and the coronal view may be adjusted separately. Details regarding the update of reconstruction planes of an intervertebral disc can be found elsewhere in the present disclosure. See, e.g., FIG. 13 and the descriptions thereof.

In some embodiments, the intervertebral disc reconstruction protocol of each of the at least one intervertebral disc is determined based on a 3D image of the spine of the subject. The reconstruction planes shown in different views (e.g., a coronal view, a sagittal view, or a transverse view) of the 3D image may be correlated as an entirety. Images showing the different views may also be 3D images. If reconstruction planes of an intervertebral disc is updated or adjusted, the directions of the intervertebral disc in the different views of the 3D image may be adjusted synchronously.

Figure 13:
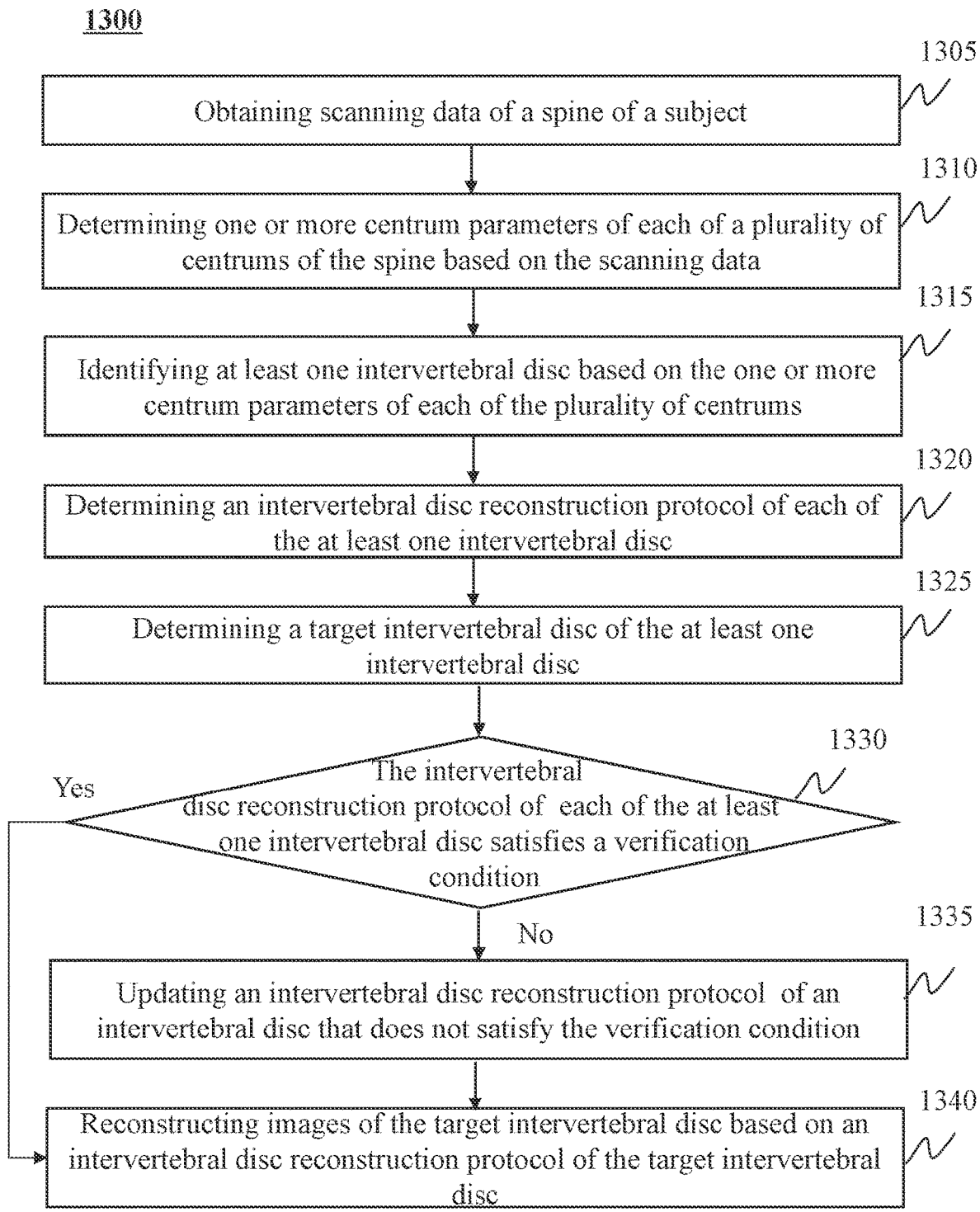
FIG. 13 is a flowchart illustrating an exemplary process for reconstructing an image of a target intervertebral disc according to some embodiments of the present disclosure.

FIG. 13 is a flowchart illustrating an exemplary process for reconstructing an image of a target intervertebral disc according to some embodiments of the present disclosure. In some embodiments, the process 1300 may be executed by the imaging system 100. For example, the process 1300 may be implemented as a set of instructions (e.g., an application) stored in a storage device (e.g., the storage device 130). The modules described in FIG. 4 and/or the processor 210 may execute the set of instructions and may accordingly be directed to perform the process 1300. The operations of the illustrated process presented below are intended to be illustrative. In some embodiments, the process 1300 may be accomplished with one or more additional operations not described and/or without one or more of the operations discussed. Additionally, the order of the operations of process 1300 illustrated in FIG. 13 and described below is not intended to be limiting.

In 1305, the processing device 120 (e.g., the obtaining module 410 or the processor 210) may obtain scanning data of a spine of a subject.

In 1310, the processing device 120 (e.g., the spine parameter determination module 420 or the processor 210) may determine one or more centrum parameters of each of a plurality of centrums of the spine based on the scanning data.

In 1315, the processing device 120 (e.g., the spine parameter determination module 420 or the processor 210) may identify at least one intervertebral disc based on the one or more centrum parameters of each of the plurality of centrums.

In 1320, the processing device 120 (e.g., the reconstruction protocol determination module 430 or the processor 210) may determine an intervertebral disc reconstruction protocol of each of the at least one intervertebral disc.

In 1325, the processing device 120 (e.g., the reconstruction module 440 or the processor 210) may determine a target intervertebral disc of the at least one intervertebral disc.

In some embodiments, the operations 1305 through 1325 may be similar to or the same as the operations 510 through 550 of the process 500 illustrated in FIG. 5, the descriptions of which are not repeated here.

In 1330, the processing device 120 (e.g., the processing device 120 (e.g., the reconstruction protocol determination module 430 or the processor 210) may determine whether the intervertebral disc reconstruction protocol of each of the at least one intervertebral disc satisfies a verification condition.

The verification condition may provide a verification as to whether the intervertebral disc reconstruction protocol of each of the at least one intervertebral disc is correct or acceptable. In some embodiments, the verification condition may be obtained from a user (e.g., a doctor, a technician, etc.). For example, upon receiving the intervertebral disc reconstruction protocol of each of the at least one intervertebral disc, the user may check the at least one intervertebral disc reconstruction protocol, e.g., by viewing a range and/or directions of each of the at least one intervertebral disc in one or more images of the spine of the subject. In some embodiments, the verification condition may be determined by the imaging system 100. For example, the imaging system 100 may provide various standards and/or algorithms that serve as the verification condition. The standards and/or algorithms may relate to the parameters or settings related to the intervertebral disc reconstruction protocol of each of the at least one intervertebral disc. For illustration purposes, the imaging system 100 may provide a range of values for each of the one or more intervertebral disc parameters of a specific intervertebral disc (e.g., the intervertebral disc L4-L5). If values of the one or more intervertebral disc parameters of the specific intervertebral disc are in the range, the imaging system 100 may determine that the intervertebral disc reconstruction protocol of the specific intervertebral disc satisfies the verification condition. Otherwise, the imaging system 100 may determine that the intervertebral disc reconstruction protocol of the specific intervertebral disc does not satisfy the verification condition.

If all the intervertebral disc reconstruction protocol(s) of the at least one intervertebral disc satisfy the verification condition, the process 1300 may proceed to 1340. If an intervertebral disc reconstruction protocol of an intervertebral disc does not satisfy the verification condition, the process 1300 may proceed to 1335 to update the intervertebral disc reconstruction protocol of the intervertebral disc.

In 1335, the processing device 120 (e.g., the processing device 120 (e.g., the reconstruction protocol determination module 430 or the processor 210) may update an intervertebral disc reconstruction protocol of an intervertebral disc that does not satisfy the verification condition.

The intervertebral disc reconstruction protocol of the intervertebral disc may be updated by adjusting image reconstruction parameters and/or one or more intervertebral disc parameters of the intervertebral disc. In some embodiments, the update of the intervertebral disc reconstruction protocol may be performed based on a user instruction. In some embodiments, the user may provide a user instruction for adjusting the values of the image reconstruction parameters and/or one or more intervertebral disc parameters of the intervertebral disc manually via an interface of the terminal device 140. Referring to FIG. 6, arrows attached on different sides of the rectangular boxes denoting the regions including the centrums and intervertebral discs may be used to adjust the directions and the ranges of the intervertebral discs. For example, if a direction of an intervertebral disc needs to be adjusted, the user may adjust the direction of the intervertebral disc by dragging at least one first arrow (e.g., an arrow in a length direction of the rectangular box) attached on a side of the rectangular box of the intervertebral disc through the interface. The rectangular box may rotate around a center point of the intervertebral disc such that the intervertebral disc may be adjusted to a desired direction. As another example, if a range of an intervertebral disc needs to be adjusted, the user may adjust the range of the intervertebral disc by dragging at least one second arrow (e.g., an arrow in a width direction of the rectangular box) attached on a side of the rectangular box of the intervertebral disc through the interface. A width of the rectangular box may be changed, such that the range of the intervertebral disc may be adjusted.

In some embodiments, the processing device 120 may update the intervertebral disc reconstruction protocol of the intervertebral disc automatically. In some embodiments, the processing device 120 may adjust the intervertebral disc reconstruction protocol of the intervertebral disc by performing the operations in 1330 and 1335 in a plurality of iterations. For example, in each of the plurality of iterations, the processing device 120 may increase or decrease the value of at least one of the image reconstruction parameters and/or one or more intervertebral disc parameters of the intervertebral disc by a certain value.

In 1340, the processing device 120 (e.g., the reconstruction module 440 or the processor 210) may reconstruct images of the target intervertebral disc based on an intervertebral disc reconstruction protocol of the target intervertebral disc.

If the intervertebral disc reconstruction protocol of the target intervertebral disc is updated, the processing device 120 may reconstruct images of the target intervertebral disc based on the updated intervertebral disc reconstruction protocol of the target intervertebral disc. In some embodiments, the processing device 120 may further generate a report based on the images of the target intervertebral disc, and display the report on a screen of a terminal device (e.g., the screen 160). By verifying the intervertebral disc reconstruction protocol of each of the at least one intervertebral disc, the accuracy of the imaging of the intervertebral disc may be improved efficiently.

FIG. 14 is a schematic diagram of an exemplary processing device according to some embodiments of the present disclosure. The computing device 1412 may facilitate the implementation of the processes or operations provided in the present disclosure. The computing device 1412 illustrated in FIG. 14 is merely an example, but not intended to limit the scope of the present disclosure.

As shown in FIG. 14, the computing device 1412 may be implemented by a computing device of general purposes. The computing device 1412 may include but are not limited to one or more processors 1416, a system memory 1428, and a bus 1418 that connects elements or components of the computing device 1412, such as the system memory 1428, the one or more processors 1416, etc.

The bus 1418 may represent one or more of several types of bus structures, including a memory bus, a memory controller, peripheral bus, an accelerated graphics port, the one or more processors 1416, or a local bus using any of a variety of bus structures. For example, the bus structures may include but not limited to, an Industry Standard Architecture (ISA) bus, a Micro Channel Architecture (MAC) bus, an Enhanced ISA Bus, a Video Electronics Standards Association (VESA) local bus, a peripheral component interconnects (PCI) bus, etc.

The computing device 1412 may include a variety of computer readable media. The computer readable media may be any available media including volatile or non-volatile media, removable or non-removable media, etc., that may be accessible by the computing device 1412.

The system memory 1428 may include computer readable media in a form of volatile memory, for example, a random access memory (RAM) 1430 and/or a read-only memory (ROM) 1432. The computing device 1412 may further include other removable/non-removable or volatile/non-volatile computer system storage media. Merely by ways of example, a storage device 1434 may be non-removable, non-volatile magnetic media (not shown in the figure, commonly referred to as a "hard disk drive") for reading and writing. Although not shown in FIG. 14, a disk drive for reading and writing to a removable non-volatile disk (such as a "floppy disk") and a removable non-volatile disk (such as a CD-ROM, a DVD-ROM, or other optical media) may be provided. In these cases, each drive may be coupled to the bus 1418 via one or more data medium ports. The system memory 1428 may include at least one program product having a set (e.g., at least one) of program modules configured to implement the functions provided in the above embodiments of the present disclosure.

A program/utility tool 1440 having a set (at least one) of program modules 1442, which may be stored, for example, in the memory 1428. The program modules 1442 may include but not limited to, an operating system, one or more applications, other program modules, or program data. Each or a combination of one or more of the above listed program modules may have a network environment implementation. The program module 1442 may perform the functions and/or methods provided in the described embodiments of the present disclosure.

The computing device 1412 may also be in communication with one or more external devices 1414 (e.g., a keyboard, a pointing device, a display 1424, etc.), one or more devices that enable a user to interact with the computing device 1412, and/or any devices (e.g., a network card, a modem, etc.) that enable the computing device 1412 to communicate with one or more other computing devices. The communication may be realized via an input/output (I/O) interface 1422. Also, the computing device 1412 may also communicate with one or more networks (e.g., a local area network (LAN), a wide area network (WAN), and/or a public network, such as the Internet) through a network adapter 1420. As shown in the figure, the network adapter 1420 may communicate with other modules of computing device 1412 via the bus 1418. It should be understood that, other hardware and/or software modules may be utilized in combination with the computing device 1412, including but not limited to microcode, device drivers, redundant processing units, external disk drive arrays, RAID systems, Tape drives, or data backup storage systems.

The one or more processors 1416 may implement, by running a program stored in the system memory 1428, various functional applications and/or data processing, for example, a method of medical imaging as provided in some embodiments of the present disclosure. According to an aspect of the present disclosure, the method may include obtaining scanning data of a spine of a subject. The method may also include determining one or more centrum parameters of each of a plurality of centrums of the spine based on the scanning data. The method may also include identifying at least one intervertebral disc based on the one or more centrum parameters of each of the plurality of centrums, each of the at least one intervertebral disc being between a pair of neighboring centrums of the plurality of centrums, and determining an intervertebral disc reconstruction protocol of each of the at least one intervertebral disc, wherein the intervertebral disc reconstruction protocols of the at least one intervertebral disc relate to multi-planar reconstruction (MPR). The method may further include determining a target intervertebral disc of the at least one intervertebral disc, and reconstructing an image of the target intervertebral disc based on an intervertebral disc reconstruction protocol of the target intervertebral disc.

Those skilled in the art may understand that the one or more processors 1416 may also implement technical solutions of the exposure process control method provided by any embodiments of the present disclosure.

The present disclosure may further provide a computer readable storage medium storing computer programs. When the computer programs are executed by a processor, operations of classification determination of a structure of a subject in an image provided in the present disclosure may be implemented. According to an aspect of the present disclosure, the operations may include obtaining scanning data of a spine of a subject. The operations may also include determining one or more centrum parameters of each of a plurality of centrums of the spine based on the scanning data. The operations may also include identifying at least one intervertebral disc based on the one or more centrum parameters of each of the plurality of centrums, each of the at least one intervertebral disc being between a pair of neighboring centrums of the plurality of centrums, and determining an intervertebral disc reconstruction protocol of each of the at least one intervertebral disc, wherein the intervertebral disc reconstruction protocols of the at least one intervertebral disc relate to multi-planar reconstruction (MPR). The operations may further include determining a target intervertebral disc of the at least one intervertebral disc, and reconstructing an image of the target intervertebral disc based on an intervertebral disc reconstruction protocol of the target intervertebral disc.

It should be noted that the computer programs stored in the computer readable storage medium may not limited to the methods or operations provided above, other methods or operations related to the automated positioning of the subject may also be provided.

Having thus described the basic concepts, it may be rather apparent to those skilled in the art after reading this detailed disclosure that the foregoing detailed disclosure is intended to be presented by way of example only and is not limiting.

Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method implemented on a computing device having a processor and a computer-readable storage device, the method comprising:
   obtaining scanning data of a spine of a subject;
   determining one or more centrum parameters of each of a plurality of centrums of the spine based on the scanning data;
   identifying at least one intervertebral disc based on the one or more centrum parameters of each of the plurality of centrums, each of the at least one intervertebral disc being between a pair of neighboring centrums of the plurality of centrums;
   determining an intervertebral disc reconstruction protocol of each of the at least one intervertebral disc, wherein the intervertebral disc reconstruction protocols of the at least one intervertebral disc relate to multi-planar reconstruction (MPR), includes:
      determining whether the intervertebral disc reconstruction protocol of each of the at least one intervertebral disc satisfies a verification condition, wherein the verification condition provides a verification as to whether the intervertebral disc reconstruction protocol of each of the at least one intervertebral disc is correct or acceptable; and
      in response to determining that the intervertebral disc reconstruction protocol of an intervertebral disc does not satisfy the verification condition,
         updating the intervertebral disc reconstruction protocol of the intervertebral disc;
   determining a target intervertebral disc of the at least one intervertebral disc; and
   reconstructing one or more images of the target intervertebral disc based on an intervertebral disc reconstruction protocol of the target intervertebral disc.

2. The method of claim 1, wherein the scanning data includes computed tomography (CT) data or magnetic resonance (MR) data.

3. The method of claim 1, wherein the one or more centrum parameters of each of the plurality of centrums of the spine include a center point and a label of the centrum.

4. The method of claim 1, wherein the determining an intervertebral disc reconstruction protocol of each of the at least one intervertebral disc includes:
   for each of the at least one intervertebral disc,
   determining one or more intervertebral disc parameters of the intervertebral disc; and
   determining the intervertebral disc reconstruction protocol of the intervertebral disc based on image reconstruction parameters and the one or more intervertebral disc parameters of the intervertebral disc.

5. The method of claim 4, wherein the determining one or more intervertebral disc parameters of the intervertebral disc includes:
   obtaining coordinates of elements of the intervertebral disc;
   determining a center point, at least two directions, and a range of the intervertebral disc based on the coordinates of elements of the intervertebral disc; and
   determining a label of the intervertebral disc based on labels of a pair of neighboring centrums, the intervertebral disc being located between the pair of neighboring centrums.

6. The method of claim 5, wherein the intervertebral disc reconstruction protocol of each of the at least one intervertebral disc relates to at least one of the label, the range, the center point, or the at least two directions of the intervertebral disc, a slice thickness, a slice count, or a reconstruction dimension.

7. The method of claim 1, further including:
   transmitting the reconstructed images of the target intervertebral disc to a terminal device;
   receiving diagnosis information from the terminal device; and
   generating a report regarding the target intervertebral disc based on the diagnosis information and the reconstructed images of the target intervertebral disc.

8. A system, comprising:
   at least one storage medium including a set of instructions; and
   at least one processor configured to communicate with the at least one storage medium, wherein when executing the set of instructions, the at least one processor is configured to direct the system to perform operations including:
   obtaining scanning data of a spine of a subject;
   determining one or more centrum parameters of each of a plurality of centrums of the spine based on the scanning data;
   identifying at least one intervertebral disc based on the one or more centrum parameters of each of the plurality of centrums, each of the at least one intervertebral disc being between a pair of neighboring centrums of the plurality of centrums;
   determining an intervertebral disc reconstruction protocol of each of the at least one intervertebral disc, wherein the intervertebral disc reconstruction protocols of the at least one intervertebral disc relate to multi-planar reconstruction (MPR), includes:
      determining whether the intervertebral disc reconstruction protocol of each of the at least one intervertebral disc satisfies a verification condition, wherein the verification condition provides a verification as to whether the intervertebral disc reconstruction protocol of each of the at least one intervertebral disc is correct or acceptable; and
      in response to determining that the intervertebral disc reconstruction protocol of an intervertebral disc does not satisfy the verification condition,
         updating the intervertebral disc reconstruction protocol of the intervertebral disc;
   determining a target intervertebral disc of the at least one intervertebral disc; and
   reconstructing one or more images of the target intervertebral disc based on an intervertebral disc reconstruction protocol of the target intervertebral disc.

9. The system of claim 8, wherein the scanning data includes computed tomography (CT) data or magnetic resonance (MR) data.

10. The system of claim 8, wherein the one or more centrum parameters of each of the plurality of centrums of the spine include a center point and a label of the centrum.

11. The system of claim 8, wherein the determining an intervertebral disc reconstruction protocol of each of the at least one intervertebral disc includes:

for each of the at least one intervertebral disc,
determining one or more intervertebral disc parameters of the intervertebral disc; and
determining the intervertebral disc reconstruction protocol of the intervertebral disc based on image reconstruction parameters and the one or more intervertebral disc parameters of the intervertebral disc.

12. The system of claim 11, wherein the determining one or more intervertebral disc parameters of the intervertebral disc includes:
obtaining coordinates of elements of the intervertebral disc;
determining a center point, at least two directions, and a range of the intervertebral disc based on the coordinates of elements of the intervertebral disc; and
determining a label of the intervertebral disc based on labels of a pair of neighboring centrums, the intervertebral disc being located between the pair of neighboring centrums.

13. The system of claim 12, wherein the intervertebral disc reconstruction protocol of each of the at least one intervertebral disc relates to at least one of the label, the range, the center point, or the at least two directions of the intervertebral disc, a slice thickness, a slice count, or a reconstruction dimension.

14. A non-transitory readable medium, comprising at least one set of instructions, wherein when executed by at least one processor of a computing device, the at least one set of instructions directs the at least one processor to perform a method, the method comprising:
obtaining scanning data of a spine of a subject;
determining one or more centrum parameters of each of a plurality of centrums of the spine based on the scanning data;
identifying at least one intervertebral disc based on the one or more centrum parameters of each of the plurality of centrums, each of the at least one intervertebral disc being between a pair of neighboring centrums of the plurality of centrums;
determining an intervertebral disc reconstruction protocol of each of the at least one intervertebral disc, wherein the intervertebral disc reconstruction protocols of the at least one intervertebral disc relate to multi-planar reconstruction (MPR) includes:
determining whether the intervertebral disc reconstruction protocol of each of the at least one intervertebral disc satisfies a verification condition, wherein the verification condition provides a verification as to whether the intervertebral disc reconstruction protocol of each of the at least one intervertebral disc is correct or acceptable; and
in response to determining that the intervertebral disc reconstruction protocol of an intervertebral disc does not satisfy the verification condition,
updating the intervertebral disc reconstruction protocol of the intervertebral disc;

determining a target intervertebral disc of the at least one intervertebral disc; and
reconstructing one or more images of the target intervertebral disc based on an intervertebral disc reconstruction protocol of the target intervertebral disc.

15. The non-transitory readable medium of claim 14, wherein the scanning data includes computed tomography (CT) data or magnetic resonance (MR) data.

16. The non-transitory readable medium of claim 14, wherein the determining an intervertebral disc reconstruction protocol of each of the at least one intervertebral disc includes:
for each of the at least one intervertebral disc,
determining one or more intervertebral disc parameters of the intervertebral disc; and
determining the intervertebral disc reconstruction protocol of the intervertebral disc based on image reconstruction parameters and the one or more intervertebral disc parameters of the intervertebral disc.

17. The method of claim 1, wherein the identifying at least one intervertebral disc based on the one or more centrum parameters of each of the plurality of centrums includes:
determining at least one region in one or more images of the spine, wherein each of the at least one region including an intervertebral disc;
obtaining, an intervertebral disc segmentation model;
identifying, based on the intervertebral disc segmentation model, the intervertebral disc from each of the at least one region.

18. The system of claim 8, wherein the determining one or more centrum parameters of each of a plurality of centrums of the spine based on the scanning data includes:
obtaining a centrum positioning model;
identifying, based on the centrum positioning model, the plurality of centrums of the spine, and/or the one or more centrum parameters of each of the plurality of centrums.

19. The system of claim 8, wherein the identifying at least one intervertebral disc based on the one or more centrum parameters of each of the plurality of centrums includes:
determining at least one region in one or more images of the spine, wherein each of the at least one region including an intervertebral disc;
obtaining an intervertebral disc segmentation model;
identifying, based on the intervertebral disc segmentation model, the intervertebral disc from each of the at least one region.

20. The system of claim 8, wherein the verification condition relates to one or more intervertebral disc parameters of each of the at least one intervertebral disc, wherein the one or more intervertebral disc parameters of each of the at least one intervertebral disc include at least one of a label, a range, a center point, at least two directions, or an area of the each of the at least one intervertebral disc.

* * * * *